(12) United States Patent
Chan et al.

(10) Patent No.: US 11,216,063 B2
(45) Date of Patent: Jan. 4, 2022

(54) VIRTUAL REALITY APPARATUS

(71) Applicant: SMILEYSCOPE PTY. LTD., Melbourne (AU)

(72) Inventors: Evelyn Chan, Box Hill (AU); Paul Leong, Box Hill (AU)

(*) Notice: Subject to any disclaimer, the term of this patent is extended or adjusted under 35 U.S.C. 154(b) by 0 days.

(21) Appl. No.: 16/630,362

(22) PCT Filed: Jul. 13, 2018

(86) PCT No.: PCT/AU2018/050732
§ 371 (c)(1),
(2) Date: Jan. 10, 2020

(87) PCT Pub. No.: WO2019/010545
PCT Pub. Date: Jan. 17, 2019

(65) Prior Publication Data
US 2020/0233485 A1    Jul. 23, 2020

(30) Foreign Application Priority Data

Jul. 13, 2017  (AU) ................................ 2017902751

(51) Int. Cl.
*G06F 3/01* (2006.01)
*A61M 21/02* (2006.01)
*G06F 3/0488* (2013.01)
*H04M 1/05* (2006.01)
(Continued)

(52) U.S. Cl.
CPC ............. *G06F 3/011* (2013.01); *A61M 21/02* (2013.01); *G06F 3/0488* (2013.01); *H04M 1/05* (2013.01);
(Continued)

(58) Field of Classification Search
CPC ......... G06F 3/011; G06F 3/0488; H04M 1/05
See application file for complete search history.

(56) References Cited

U.S. PATENT DOCUMENTS 9,131,205 B2   9/2015  Gillies et al.
9,406,096 B2   8/2016  Bucolo et al.
(Continued)

FOREIGN PATENT DOCUMENTS

| CN | 103228316 | 7/2013 |
| WO | 2013/054257 | 4/2013 |
| WO | 2017066340 | 4/2017 |

OTHER PUBLICATIONS

Dargar et al., Towards immersive virtual reality (iVR): a route to surgical expertise, Feb. 2, 2015, Journal of Computational Surgery, DOI 10.1186/s40244-015-0015-8, pp. 1-26 (Year: 2015).*

(Continued)

*Primary Examiner* — Samantha (Yuehan) Wang
(74) *Attorney, Agent, or Firm* — McDonnell Boehnen Hulbert & Berghoff LLP

(57) ABSTRACT

Provided is a virtual reality (VR) device, system and framework for generating VR continuum experience choreographed to a physical procedure incorporating at least one procedural action associated with a physical sensation and potentially inducing an anxiety or pain response. The VR continuum experience can modify perceptions of pain and anxiety associated with the procedure. The virtual reality device is configured to allow device control via a device user interface accessible to an operator other than the wearer (i.e. a medical practitioner), to allow the operator to control device calibration and virtual reality (VR) experience start while the apparatus is worn by the wearer, and to provide one or more VR experiences each associated with a physical procedure.

13 Claims, 17 Drawing Sheets

(51) Int. Cl.
  *H04M 1/72406* (2021.01)
  *H04M 1/72409* (2021.01)
  *H04M 1/72463* (2021.01)
  *A61M 21/00* (2006.01)
  *G06F 3/0482* (2013.01)

(52) U.S. Cl.
  CPC ... *H04M 1/72406* (2021.01); *H04M 1/72409* (2021.01); *H04M 1/72463* (2021.01); *A61M 2021/005* (2013.01); *A61M 2021/0016* (2013.01); *A61M 2021/0022* (2013.01); *A61M 2021/0027* (2013.01); *G06F 3/0482* (2013.01)

(56) References Cited

U.S. PATENT DOCUMENTS

| | | | |
|---|---|---|---|
| 9,694,155 B2 | 7/2017 | Panova et al. | |
| 2010/0079356 A1* | 4/2010 | Hoellwarth | G06F 3/16 345/8 |
| 2015/0306340 A1* | 10/2015 | Giap | G16H 20/40 600/301 |
| 2016/0350609 A1* | 12/2016 | Mason | G06T 19/003 |

OTHER PUBLICATIONS

The European Search Report (ESR) for corresponding 18831539 dated Jun. 9, 2020, pp. 1-10.

Malloy, K.M. et al., "The Effectioveness of Virtual Reality Distraction for Pain Reduction, a Systematic Review", Clinicakl Psychology Review, Pergamon Press US, vol. 30, No. 8, Dec. 1, 2010, pp. 1011-1018, XP027395077.

The International Search Report (ISR) with Written Opinion for PCT/AU2018/050732 dated Sep. 26, 2018, pp. 1-13.

Nilsson, Stefan et al. "The use of Virtual Reality for needle-related procedural pain and distress in children and adolescents in a paediatric oncology unit" European Journal of Oncology Nursing 13 (2009) pp. 102-109.

Kind VR "Virtual Reality Therapy" Jan. 18, 2017 as per wayback engine <https://web.archive.org/web/20170118114615/https://www.kindvr.com/> Retrieved on Jan. 10, 2020.

The International Preliminary Report on Patentability (IPRP) for PCT/AU2018/050732 dated Jun. 11, 2019, pp. 1-24.

Untranslated first office action dated Jun. 29, 2021 issued on corresponding Chinese patent application No. 201880046729.9.

* cited by examiner

| Scenario A (prior art): one user with prior art (gamer) | Scenario B: two users using a prior art VR device (e.g. healthcare context) | |
|---|---|---|
| One operator/user  | Operator (e.g. clinician/teacher)  | End-user (e.g. patient/student)  |
| Turns on phone | Turns on phone | |
| Puts phone into VR headset | Puts phone into VR headset<br>– Risk of breakage when taking phone in/out | |
| Selects VR mode | Selects VR mode<br>– Takes time to select/boot into VR | |
| Puts on headset | Puts on headset<br>– Operator does not want to wear/contaminate headset but is required to in order to select/control the experience for end-user | |
| Calibrates, make visual adjustments | Calibrates, make visual adjustments<br>– Additional step takes time | |
| Selects VR app (via button or controller) | Selects VR app (via button/controller)<br>– Additional step takes time | |
| Selects VR sub-app (via button/controller) | Selects VR sub-app (via button/controller) | |
|  |  | End-user wears VR headset<br>Re-calibrate for end-user<br>– May not be able to make their own visual adjustments |
| Play VR experience |  | Play VR experience<br>– May easily or inadvertently stop/pause/exit VR sub-app |
| End VR experience |  | Experience ends<br>– End-user may not have capacity to re-play or exit experience |
|  | Operator puts on headset to exit or re-play experience<br>– Needs to put on headset again to view/make selection | |

Figure 1

| Scenario C: two users with VR device modifications in accordance with an embodiment of the invention (e.g. healthcare context) ||
|---|---|
| Operator<br>(e.g. clinician/teacher) | End-user<br>(e.g. patient/student) |
| The device can be always on<br>Permanently secured into headset for use<br>✓ Lower leakage risk<br><br>Custom loader: directly boots to VR<br>✓ Saves time, always ready<br>✓ Same supervisory start-up used anywhere<br>Touchscreen selection<br>✓ Operator can fully control VR experience via touchscreen or buttons<br>✓ Does not need to put on headset to select VR application | |
| | End-user wears VR headset<br>✓ Custom-made headset optimally developed for clinical environment<br>VR experience plays<br>✓ Buttons associated access for specific app/in-clinic<br>Experience ends<br>✓ Loops as required to continue experience |
| Operator calibrates/starts VR sub-app<br>✓ Specific button combo simultaneously start/stop/calibrate | |
| Operator can stop and re-calibrate<br>✓ Ready immediately for the next end user | |

| Real sensation | Intensity (adjustable) | Transposed: Underwater examples | Transposed: Outdoors examples |
|---|---|---|---|
| Tactile: prick or scratch | Very intense — Very gentle; Very painful — Not painful | Poked coral; Nibbled by a fish; Touched a starfish | Pricked by rose thorn; Poked by a pine needle; Touched a shrub |
| Tactile: wipe | Very intense — Very gentle; Very painful — Not painful | Brushed against coral; Touched sea sponge; Washed by gentle waves | Licked by cat; Rubbed by cat; Stroke by cat's tail |
| Tactile: push in or insert | Very intense — Very gentle; Very painful — Not painful | Bumped by a hammerhead shark; Nuzzled by a dolphin; Swam into a fish | Bumping into a tree branch; Pushing against camping pole; Testing a marshmallow stick |

Figure 13

|  | Education | Observation | Practice | Assessment | Clinician Review | Preparation | Procedure | Evaluation |
|---|---|---|---|---|---|---|---|---|
| Child | VR or 2D | VR or 2D | VR, AR or 2D | VR, AR or 2D |  | VR, AR or 2D | VR or AR | VR, AR, 2D or in-person |
| Family |  |  | Able to modulate | Able to modulate |  |  | Able to modulate |  |
| Clinician |  |  | Able to modulate |  | VR, AR or 2D |  | Able to modulate |  |
| Rationale | Enables the child and family to understand:<br>• Rationale for the procedure<br>• What to expect<br>• What they need to do<br>• Try VR | Enable the child and family to:<br>• Select a character<br>• Watch what will happen to that character undergoing the procedure | Enable the child to:<br>• Acclimatise to the procedure room<br>• Play and explore the area<br>• Simulate the procedure<br>• Practice with elements adjusted as required (e.g. sound volume) | Enables the child to undergo a mock procedure to assess their needs:<br>• Simulates procedure<br>• Monitors response and ability to comply with procedure | Enables clinician to review patient's response in simulated environment:<br>• Assess suitability for the procedure<br>• Plan the strategy and approach best suited to the child's needs | Prepares the child and family for the procedure:<br>• Supports pre-procedural anxiety<br>• Reminds the child and family about important aspects of the procedure<br>• Distracts child while waiting | Supports the child during the procedure:<br>• Distract<br>• Reframe or transpose perceptions<br>• Reduce pain, anxiety, distress<br>• Increase cooperation | All participants are able to provide feedback on the experience:<br>• Assess what worked and what could be improved<br>• Clarify preferences<br>• Determine future needs |

Figure 15

| | Education | Observation | Practice | Assessment | Clinician Review | Preparation | Procedure | Evaluation |
|---|---|---|---|---|---|---|---|---|
| Child | 2D video seen at home | 2D video seen at home | VR, AR or 2D *Able to modulate* | VR *Able to modulate* | | VR in the waiting room | VR *Able to modulate* | |
| Family | | | | | | | | |
| Clinician | | | | | 2D review | | | In person evaluation post-procedure |
| Description of activity | Enables the child and family to understand: <br>• Why the child is getting an MRI <br>• What the MRI scan will involve, including a needle to inject contrast <br>• They will need to stay still in the MRI scanner for 20 minutes | Enable the child and family to: <br>• Select a character <br>• Watch the character go through the procedure from start to finish | Enable the child to practice at home: <br>• Acclimatise to the MRI room <br>• Explore the MRI room <br>• Simulate the procedure <br>• Practice with softer MRI sounds, which gradually become louder if the child is tolerating the simulation | Enables the child to undergo a mock procedure to assess their needs: <br>• Simulate the needle procedure, IV contrast injection and MRI scan <br>• Monitors response and sensors assess whether the child could comply with procedure | Enables the clinician to review patient's response to the simulation: <br>• Assess the child's ability to stay still for the sufficient scanning period <br>• Plan the approach – e.g. awake scan or sedation level required | Prepares the child and family for the intravenous needle for contrast: <br>• Supports pre-procedural anxiety <br>• Enables insertion of the intravenous needle <br>• Distracts child while waiting | Supports the child during the MRI scan: <br>• Distract <br>• Reframe or transpose perceptions such as the loud noises <br>• Reduce pain, anxiety, distress <br>• Increase cooperation and staying still during the scan | The child and family report what worked well, could be improved, and preferences for future procedures. The clinician records the approach used (e.g. light sedation, reduced sound, calming VR) and any modifications recommended for future procedures |

Figure 16

Patient-controlled variables

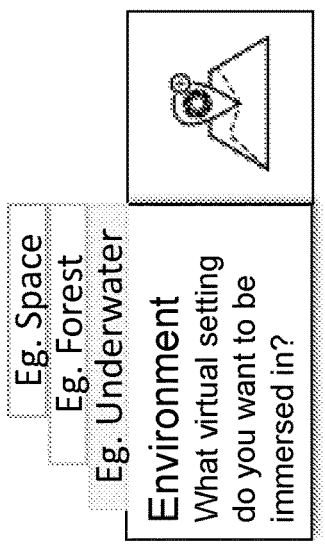

Eg. Space
Eg. Forest
Eg. Underwater

Environment
What virtual setting do you want to be immersed in?

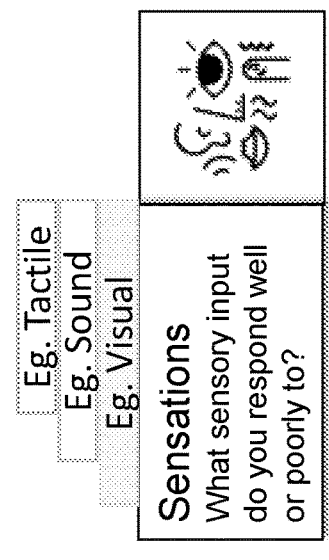

Eg. Tactile
Eg. Sound
Eg. Visual

Sensations
What sensory input do you respond well or poorly to?

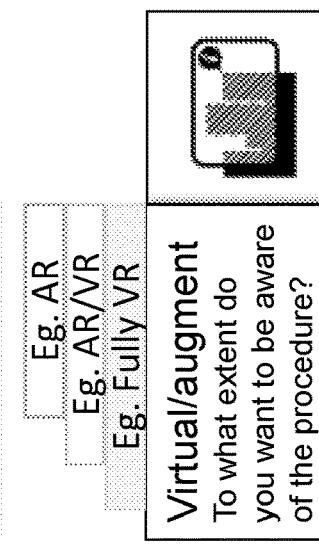

Eg. AR
Eg. AR/VR
Eg. Fully VR

Virtual/augment
To what extent do you want to be aware of the procedure?

Resource library to customise experience

Clinician-controlled variables

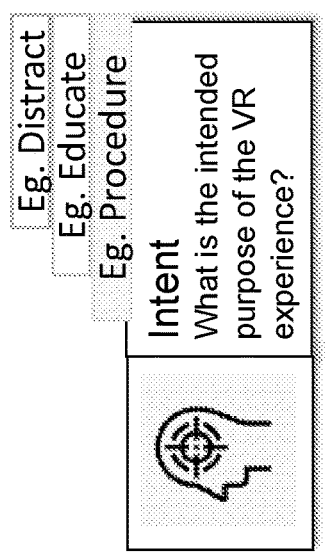

Eg. Distract
Eg. Educate
Eg. Procedure

Intent
What is the intended purpose of the VR experience?

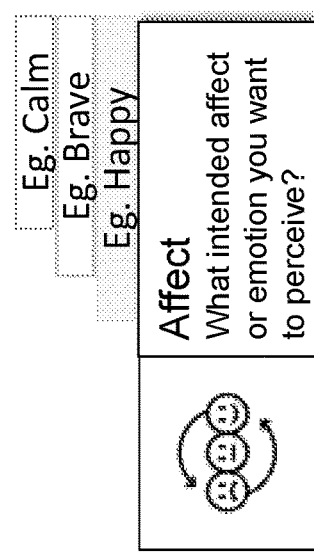

Eg. Calm
Eg. Brave
Eg. Happy

Affect
What intended affect or emotion you want to perceive?

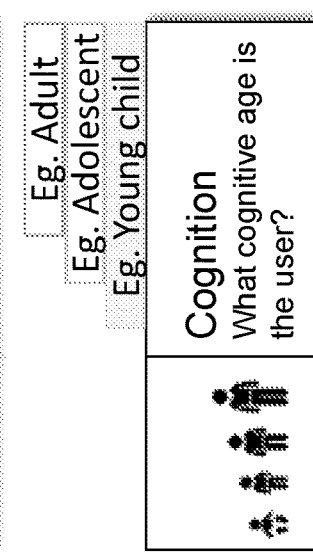

Eg. Adult
Eg. Adolescent
Eg. Young child

Cognition
What cognitive age is the user?

Figure 18

| Step | Venepuncture (blood draw) | Lumbar puncture (spinal fluid draw) | Nitrous gas anaesthetic |
|---|---|---|---|
| 1 | Introduction | Introduction | Introduction |
| 2 | Gather equipment | Gather equipment | Gather equipment |
| 3 | Apply tourniquet | Position patient | Apply mask to patient |
| 4 | Clean skin | Feel spine | Encourage deep breaths |
| 5 | Insert needle | Clean skin | Monitor while sedated |
| 6 | Draw blood | Insert needle | |
| 7 | Remove needle | Remove stylet | |
| 8 | Apply bandaid | Catch fluid | |
| 9 | | Remove needle | |

Figure 19

| Step | (Taken from medical procedure resource library) | | (Matched to VR transpositions resource library, with a selection of different VR environments) | |
|---|---|---|---|---|
| | Nitrous gas anaesthetic 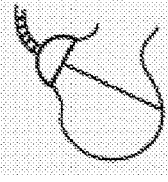 | | VR underwater transposition 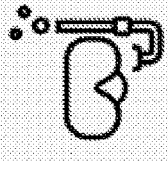 | VR space transposition 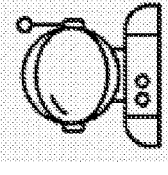 |
| 1 | Introduction | | User is on boat in a tropical reef | User has beautiful city views from the NASA headquarters |
| 2 | Gather equipment | | Prepares to go scuba diving | Prepares to go on a space adventure |
| 3 | Apply mask to patient | | Puts on scuba diving mask | Puts on space helmet |
| 4 | Encourage deep breaths | | Takes deep breaths to check equipment | Takes deep breaths to check equipment |
| 5 | Monitor while sedated | | Dives into the tropical reef | Effortlessly floats up into space |

Figure 20

VIRTUAL REALITY APPARATUS

CROSS-REFERENCE TO RELATED APPLICATION

This application is a U.S. national phase of International Application No. PCT/AU2018/050732, filed on Jul. 13, 2018, which claims priority to Australian Patent Application No. 2017902751, filed Jul. 13, 2017, both of which are incorporated by reference herein in their entirety.

TECHNICAL FIELD

The technical field of the invention is apparatus and applications of virtual reality.

BACKGROUND

Virtual reality is a computer technology that uses head mounted goggles with a screen in front of the wearer's eyes and optionally speakers or headphones to provide an immersive and interactive user experience simulating a user's presence in an imaginary environment. Virtual reality (VR) headset movements are tracked to allow a user to "look around" in a three dimensional virtual world.

Currently available VR devices typically include small stereoscopic displays, gyroscopes and motion sensors for movement tracking, and headphones or speakers. There are some known head mounts for smart phones to provide a VR experience using the smart phone. The smart phone is programmed with VR software utilising the device processor, display, gyroscopes, motion sensors, speakers etc. The head mount hold the smart phone in front of the wearers eyes such that the display is divided in two, one or each eye, and the smartphone software displays stereoscopic images which are perceived as three dimensional by the user.

Current applications for virtual reality include gaming applications and simulator type training. The use of VR can allow a user to feel like they are "in" the simulated environment which is attractive for the fantasy of gaming. Virtual reality can enable one's perception of events to feel "real" in the virtual environment. This can be particularly useful for training purposes, to practice skills in an environment that feels real but in which it is safe to fail.

Virtual reality is currently used to some extent for medical applications, mostly for simulation type training for medical practitioners. It is speculated that virtual reality may be able to aid in treating of patients particularly having anxiety disorders or for behavioural therapy. However, virtual reality systems developed for applications such as gaming or simulator training are typically designed for control by the wearer and not well adapted for interactive clinical situations.

SUMMARY OF THE INVENTION

According to one aspect there is provided a virtual reality device configured to be head mountable to a wearer and to allow device control via a device user interface accessible to an operator other than the wearer, to allow the operator to control device calibration and virtual reality (VR) experience start while the apparatus is worn by the wearer, and to provide one or more VR experiences each associated with a physical procedure.

The device can be configured to perform calibration for the wearer and start a VR experience in response to a single initialisation input from the operator. In one example the VR experience can be selected by the operator via the device user interface before the initialisation input. In an alternative example the VR experience is predefined.

The at least one of the one or more VR experiences can be designed to facilitate re-imagining of a physical procedure experience by the wearer.

In some embodiments the VR experience includes contextual reframing of sensations experienced by the wearer during the physical procedure.

In some embodiments the VR experience is further designed to coordinate timing of an operator for the physical procedure with the VR experience.

In some embodiments the VR experience and physical procedure timing is influenced by the wearer's interaction with the VR experience.

In some embodiments the VR experience is generated using a VR continuum experience framework comprising an order of execution for actions of a physical procedure incorporating at least one procedural action associated with a physical sensation and potentially inducing an anxiety or pain response, and for each of the procedural actions defining characteristics of a VR transposition to modify perception for the action of any one or more of pain, anxiety or presence.

In some embodiments the device comprises a mobile phone providing processing, memory, visual display, motion sensing, audio and user interface functionality and a headset supporting the mobile phone, and wherein the mobile phone is loaded with a VR software application configured to restrict functions of the mobile phone to the VR functionality while the VR software application is executing.

In an embodiment the VR software application is configured to provide a touchscreen user interface displayed concurrently with a VR experience display and the headset is configured to prevent view of the touchscreen user interface by the user.

According to another aspect there is provided a virtual reality continuum (VR) experience framework for generating a VR continuum experience choreographed to a physical procedure incorporating at least one procedural action associated with a physical sensation and potentially inducing an anxiety or pain response, the framework comprising:

an order of execution of the procedural actions; and
for each of the procedural actions defining characteristics of a VR transposition to modify perception for the action of any one or more of pain, anxiety or presence.

In some embodiments each VR transposition is defined based on the requirements of the procedure for presence and aspects of the action inducing physical sensation, and target direction for modification in one or more of presence, anxiety and pain perception.

In some embodiments a VR transposition is characterised by reframing aspects of the physical interaction in a manner which is not inconsistent with the physical sensation induced by the action and encourages altered perception of the physical sensation.

In some embodiments a VR transposition is characterised by mimicking duration and attributes of the physical sensation for choosing a representation in a VR context using an interaction which is typically associated with less pain or anxiety than the actual physical action.

In some embodiments a VR experience can be generated by selecting, from a library of VR experience components of a common theme, for each defined VR transposition a VR experience component fulfilling the characteristics of the defined VR transposition and compiling the selected VR experience components into a VR experience based on the action sequence for the procedure.

According to another aspect there is provided a virtual reality (VR) experience generation system comprising:
- a medical procedure library storing one or more sequences of procedural actions for one or more medical procedures;
- a VR transposition resource library comprising for each procedural action associated with a physical sensation and potentially inducing an anxiety or pain response, defined characteristics of a VR transposition to modify perception for the action of any one or more of pain, anxiety or presence, and a plurality of VR experience components for each defined VR transposition wherein the VR experience component fulfils the characteristics of the defined VR transposition in the context of one or more VR experience themes; and
- a VR experience compiler configured to compile a VR experience for a medical procedure by retrieving from the medical procedure library a sequence of procedural actions for the medical procedure, select from the VR transposition resource library a VR experience component for each defined VR transposition using a common VR experience theme and compiling the selected VR experience components into a VR experience based on the action sequence for the procedure.

According to another aspect there is provided a method of generating a virtual reality continuum (VR) experience choreographed to a physical procedure incorporating at least one procedural action associated with a physical sensation and potentially inducing an anxiety or pain response, the method comprising the steps of:
- determining an order of execution of the procedural actions;
- for each of the procedural actions defining characteristics of a VR transposition to modify perception for the action of any one or more of pain, anxiety or presence;
- obtaining a VR experience component for each defined VR transposition using a common VR experience theme, wherein the VR experience components fulfils the characteristics of the defined VR transposition; and
- compiling the selected VR experience components into a VR experience based on the order of execution of the procedural actions for the procedure.

Obtaining a VR experience component can comprise selecting the VR experience component from a VR transposition resource library. Alternatively or additionally obtaining a VR experience component can comprise creating a VR experience component based on the characteristics of the defined VR transposition.

BRIEF DESCRIPTION OF THE DRAWINGS

FIG. 1 shows procedural steps for two use scenarios using the same current commercially available VR system.

FIG. 2 shows procedural steps for a use scenario using an embodiment of the present invention.

FIG. 12 illustrates phases of healthcare procedures and activities/techniques corresponding to each phase.

FIG. 13 illustrates examples of physical procedures and the physiological pain level and intensity typically anticipated for these procedures.

FIG. 15 illustrates a general overview of the end to end framework for a procedure choreographed VR experience.

FIG. 16 illustrates and example of an end to end framework applied for an MRI procedure.

FIG. 18 conceptualises the clinician controlled/variable aspects procedures and VR experiences.

FIG. 19 shows the steps for three procedures which may benefit from VR (or AR) patient support.

FIG. 20 shows an example of the steps of the Nitrous gas anaesthesia procedure and corresponding VR transpositions using two alternative themes.

DETAILED DESCRIPTION

Figure 3:
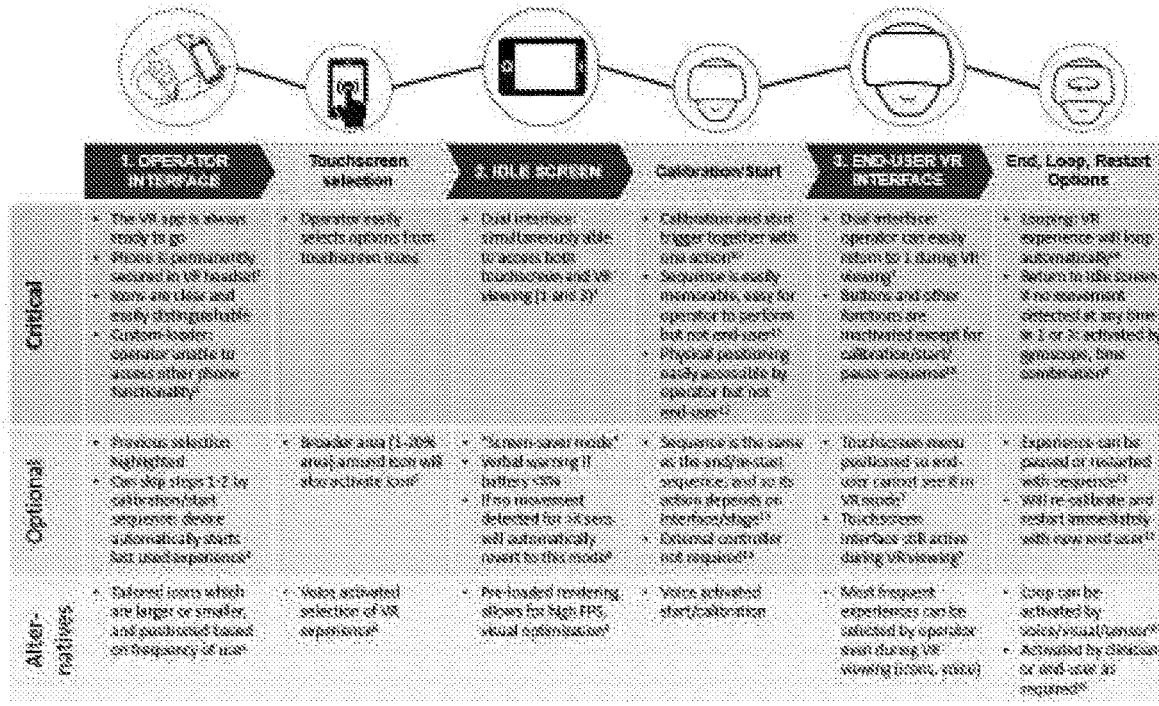
FIG. 3 shows an overview of technical features adapted for providing a dual-user VR experience.

Provided is a virtual reality device configured to be head mountable to a wearer and to allow device control via a device user interface accessible to an operator other than the wearer. The VR device is configured to allow the operator to control device calibration and virtual reality (VR) experience start while the apparatus is worn by the wearer, and to provide one or more VR experiences. The VR experiences can be designed to facilitate re-imagining of a physical procedure experience by the wearer. Examples of applications for this device and VR experiences include medical procedures for children such as giving injections or taking blood samples. However, embodiments may be applied in many different physical procedures and scenarios.

Embodiments can provide procedure specific VR experiences to support individuals undergoing these procedures. For example, to aid in managing pain and/or fear associated with medical procedures. Medical procedures (such as venepuncture—taking blood, or the insertion of an intravenous cannula) are common in healthcare. Many patients regard medical procedures involving needles as one of the most feared and painful parts of the hospital experience, and the procedure can cause significant anxiety and distress that can also extend to family. Current pain management techniques, such as local anaesthetic cream or distraction may be inadequate, resulting in a need to restrain or sedate the patient. The inventors' VR system allows users to experience an engaging and interactive three dimensional "virtual world" during such procedures, where within the context of this virtual world the user's perception of the sensations of the procedure can potentially be altered to provide an improved clinical experience. Escape into the virtual world can enable re-imagining of sensations for example to alter pain perceptions and reduce anxiety.

VR may provide an effective drug free way to reduce fear and pain associated with medical procedures. However, in order for VR to become a well adopted tool in the healthcare environment it is important that the VR experience be optimised for both the clinician and the patient. Although needle procedures are discussed as a procedure where embodiments of this VR system may be of benefit, there are many different types of procedures where VR can be beneficial to use. Procedures/actions typically associated with causing moderate to severe pain include but are not limited to: venepuncture or phlebotomy, insertion of peripheral intravenous line, insertion of urinary catheter or suprapubic aspiration, cleaning or care of excoriated skin, insertion of endotracheal tube, insertion of peripheral arterial line, removal of chest tube, insertion of peripherally inserted central catheter, lumbar puncture, endoscopy, insertion of nasojejunal tube, insertion of central venous line, intramuscular injections, manipulation and reduction of fractures and dislocations, and minor surgical procedures. Procedures/actions typically associated with causing mild to moderate pain include but are not limited to: capillary sampling, endotracheal suctioning, dressing change or removal, mobilization, subcutaneous injections, skin-prick testing, removal of endotracheal tube, removal of tape from skin, insertion of nasogastric tube, scraping or swabs (for culture or specimen), tracheotomy care, repositioning or restrapping of endotracheal tube, tracheotomy suctioning, and wound irrigation. Procedures/actions typically associated with mild pain include but are not limited to: oral or nasal suctioning, removal of peripheral intravenous line, removal of urinary catheter, removal of nasogastric tube, nasopharyngeal scraping or swabs, removal of peripheral arterial line, removal of central venous line, accessing implantable venous port, applying and removing plaster casts, and removal of sutures.

It should be noted that many of the above procedures or actions (e.g. insertion of a peripheral venous line) are 'channels' for lots of different treatments (it may be for collecting blood for testing, delivering chemotherapy, or antibiotics, etc.) so in the context of an end to end treatment more than one action or procedure associated with causing pain may be required. Further studies have shown that perceptions of pain can also be influenced by psychological factors, in particular fear and anxiety associated with the medical procedures. For example, studies with children have recorded patients recalling needle pokes as being the most painful part of a procedure even though pain level/intensity (subjectively reported by the patient using a scale of 0-10 with 0 being no pain and 10 being worst pain imaginable) for needle pokes was not as high as for other pain causes such as trauma or surgery. The perception of pain therefore appears to be influenced by the patient anxiety associated with the procedure not only the physical causes of pain. Embodiments of the VR system aim to manipulate perceptions of pain by using VR experiences designed to facilitate re-imagining of a physical procedure experience by the patient. This can include contextually reframing sensations experienced by the wearer during the physical procedure. The VR experienced is choreographed with the physical procedure to enable the patient to experience the physical sensations of the procedure in the context of the VR world (VR experience) thus modifying the patient experience resulting in reduced pain and/or anxiety. Thus, aspects of the VR system include development of the procedurally choreographed VR experiences, and modifications to VR devices for use in a clinical setting.

Historically, VR was developed for video gamers who would singularly perform all functions from selecting the experience, calibrating and starting the game whilst wearing the headset. However, there are problems with the current design for VR in dual-users scenarios, such as healthcare or education environments. This can be particularly problematic where only one user, and not the controlling person, may be wearing a VR device. For example, in healthcare and/or educational environments, often there are at least 2 users: the operator (e.g. clinician, teacher) and end-user (e.g. patient, student). Further in such instances often the wearer of the VR device may not be the individual controlling the device. An example of such as scenario is where the VR device wearer is a young child or a person who is disabled, infirm, injured or incapacitated. There may also be support users involved in the process such as parents/family, teacher's aides, other clinicians who are supporting the procedure.

Currently commercially available VR devices have not been designed to accommodate the needs or user experience of having separate operator and end-user.

It is problematic in environments such as clinical settings or classrooms if the operator has to perform multiple steps before end user use—for example if the operator has to put on the headset first to choose the VR experience before giving the headset to the user. One aspect of the present device adapts the technology to meet this need, so that the operator can easily operate the VR headset without having to execute multiple steps before end-user use. This is relevant in healthcare and educational environments where there are separate operators and end-users. Common scenarios can include:

Medical procedures
Surgical procedures
Nursing procedures
Dental procedures
VR for people with disabilities
VR therapies (e.g. phobia treatment, PTSD, autism)
Patient education (e.g. around procedures, diseases)
Education (e.g. children, students, university settings)

It should be appreciated that these types of environments may be fast-paced and where the end users may only use the VR for short periods of time. Further there may also be fast turnover of VR end users.

FIG. 1 shows procedural steps for two use scenarios using the same current commercially available VR system (such as Google Daydream or Cardboard). Scenario A shows procedural steps for a single user VR experience including setup (for example, that of a gamers). Scenario B shows procedural steps for a dual user scenario (for example a healthcare context), compared with Scenario A showing the steps required to be performed by the two different users.

Scenario A is a current common use of prior art VR where there is one user who is fully competent to operate and use the VR equipment (e.g. in a VR gaming context). Prior art (e.g. Google Daydream or Cardboard) is designed to work well in this scenario. VR has been developed with the intention for a single person to operate and be the end-user. However, Set-up takes time: assumes the user will navigate through VR library in VR while wearing the device. Typically, there are also a wide range of VR experiences to choose from and the user is able to navigate out of VR to another device function. There is also an assumption that the user will exit and watch a new experience or navigate to another device function.

Scenario B is an example of using a prior art VR device (for example the same device as for Scenario A) when there are two users—one who is the operator, and one who is the end-user (e.g. healthcare context, procedures, or with the elderly or children). In these contexts, using the prior art device is not efficient, as it involves many steps and the operator needing to wear the VR headset to intervene/ operate the VR experience before and after providing it to the end-user.

Some of the problems with using current VR design in health/education environments are summarised in the following points 1 to 4.

1. The operator and end-user of VR are usually two different people (e.g. clinician and patient) Issues using current design include:
    Poor user experience for the VR operator
    Infection control: operator does not want to wear/contaminate the headset just to select/control the experience for end-user
2. Time-intensive set-up for VR is not conducive for the rapid turnaround often required in healthcare or education: often multiple end-users using one VR headset in quick succession (e.g. a clinician may provide VR to multiple patients while the patient has blood taken, or a teacher providing a VR experience to many students).
    Often requires time-intensive adjustments: e.g. inter-pupillary distance, focal distance, etc.
3. Too many functions and options risk that the VR experience is difficult to access, and can be too easily paused/ exited unintentionally. Another problem can be unintentional changes to the VR content during a VR experience, for example, changing scenario if a button is accidentally bumped.
4. Experience runs until it is finished, then stops until further action is taken: sometimes the operator requires more time than the set experience.

The inventors have developed a modified VR device to enable streamlined user experience for dual-users (operator/ end-user). An example of procedural steps for an embodiment of the modified VR device are shown in FIG. 2, for Scenario C, a clinical use scenario where the inventors' adaptations and modifications are designed to optimise the VR user experience for two users (operator, end-user). Embodiments of the modified VR device are designed around simplifying the process for operators so that the entire process is quick and seamless. These VR device operation modifications include:

1. Designing a streamlined user experience for both the operator and end-user
    Operator has full control of the VR experience without having to wear the headset (e.g. via touchscreen, external buttons)
    End-user views and can interact with the VR experience, but is not responsible for actions such as activating/ selecting/exiting the experience
2. VR experience that is quick and easy for the operator to select and is streamlined to the clinical/educational environment:
    Incorporate calibrate and start into one single action.
    Allows for quick changes in direction, rapidly moving from one end-user to another end-user. For example, end-users may be facing different directions, and in some clinical settings (for example immunisation clinics) rapid turnover is desirable so it is desirable for calibration and start/stop to be quick and seamless. Should have minimal adjustments required.
3. Functions are limited by custom loader
    Automatically boots into VR app
    Unable to return to smartphone home screen (locked)
    Can automatically start the last experience that was previously selected
    Optionally locking out any further operator changes (for example, preventing changes to the VR experience) after initiation.
4. Looping function: VR experience continues
    Option that the end-user can re-start the experience
    If the experience is paused or there is no movement for >30 seconds the experience is paused (idle), but picks up from where it left off These dual user VR device operation modifications were developed in order to streamline VR use during clinical procedures, for example during paediatric needle procedures.

FIG. 2 shows procedural steps for a use scenario (scenario C) for of a dual user VR experience including setup using an embodiment of the invention. In this scenario the VR device is configured to enable setup of the VR experience by the operator using the device but without requiring the operator to wear the device. The device is then placed on the wearer's head (the patient) and the operator triggers calibration of the device and start of the selected VR experience. Buttons which may be conventionally enabled for control of the VR device can be disabled while the VR experience plays to reduce the risk of the wearer interfering with control of the VR device. The stop and recalibrate buttons may remain enabled to enable the operator to intervene, if necessary. Once the VR experience ends the device can be configured to automatically restart or loop the experience or a part of the experience without requiring operator intervention. For example, if further time is required to complete the procedure the VR experience can continue, repeating all or part of the experience. Features of the VR device and experience are described in further detail below with reference to FIG. 3 which provides an overview of technical features adapted for the a dual-user VR experience.

The VR device may be configured to be "always on" to avoid requiring turning on before a procedure. The device may have a movement sensitive standby mode for battery conservation. Whereby the device will enter a standby mode after a predetermined time period with no movement detected and exit the standby mode to an awake/use state in response to movement, such as a user picking up the device or resuming movement (i.e. recovering from anaesthesia).

Figure 4:
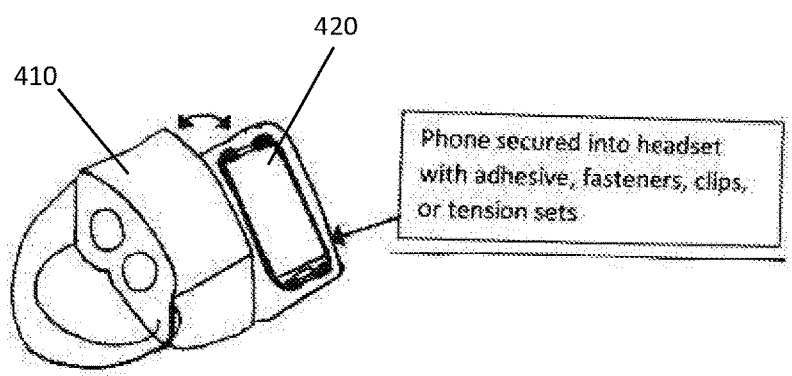
FIG. 4 shows an example of an embodiment of a VR headset.

In some embodiments the VR device may comprise a processing and display device mounted in a headset. Some examples of devices which may be used as the VR device display and processing device include mobile phones, small tablet computers, media players or similar such devices having displays and capable of executing the VR software. The headset is configured to support the device and may include structural and optical components to aid viewing the VR display. In some embodiments the display and processing device may be secured into the headset for use. An example of an embodiment is shown in FIG. 4. This embodiment comprises a headset 410 supporting a mobile phone 420. The mobile phone 420 provides processing, memory, visual display, motion sensing, audio and user interface functionality and is loaded with a VR software application configured to restrict functions of the mobile phone to the VR functionality while the VR software application is executing. The mobile phone 420 is secured into the headset for example using adhesive, fasteners, clips, or tension sets etc.

The processing and display device may be permanently secured to ensure the device cannot be stolen or removed accidentally/fall out. In some embodiments the device may be removably secured, for example to allow for cleaning of the headset without risking damage to the processing and display device. For example, the processing and display device may be sealed within a sleeve in a manner that makes it difficult to remove and reduces risk of accidental removal but allows for deliberate removal of the processing and display device. It is envisaged that in some embodiments the headset components may be disposable and the processing and display device reusable.

In one such embodiment the processing and display device may be permanently sealed into a sleeve or compartment of the headset to secure the device into the headset, requiring damage (and subsequent disposal) of the headset to remove the processing and display device. Such an embodiment may be preferred for use in a medical/surgical setting to reduce contamination risks. It is also envisaged to provide a VR device headset compatible with an autoclave to allow the headset to be sterilised similarly to surgical equipment.

It should be appreciated that embodiments of the VR device are self-contained and not required to be tethered or controlled via a remote controller or device.

Other features of the headset can include a waterproof and wipeable cover. It is also desirable that the head set is lightweight. The headset straps should be adjustable, particularly to facilitate use with children. In an embodiment the headset is provided with T-bar type three way straps to distribute weight evenly and allow the device to me more easily supported on children's heads. The device may be sized and shaped specifically for use with children. Currently VR devices are recommended for use only by children older than 10 years. Headsets are therefore not produced specifically for younger children. The inventors have found that for the present application of VR to medical procedures the short duration for typical procedures for children 4 to 11 years old (i.e. immunisations) use of VR is relatively safe with a very low side effect profile. Other modifications may include colours, patterns or decals to make the device appearance more "fun" and less threatening for children. Such modifications may not be necessary for devices designed for use with adult patients.

In other embodiments the processing and display device may be integral with the headset. Such embodiments may utilise processing and display hardware dedicated for the procedural VR application. Such embodiments may not provide other functionality such as telecommunication functionality. Alternatively, functionality such as wireless communication and data capture may be limited by requirements for the procedural VR application, for example limited to short range wireless communication restricted to the purpose of updating VR programs or downloading data collected during a VR experience. This may be desirable to reduce any one or more of the device complexity, processing, battery, and memory requirements. Such embodiments may have advantages in reducing device costs and/or reduce the likelihood of devices being stolen for other uses. Use of dedicated device hardware may also enable embodiments capable of being subjected to rigorous cleaning and/or sterilisation procedures.

The device can include a custom loader to cause the device to directly launch in VR mode on boot (turn on) or wake up from standby. This can significantly simplify and speed up the set-up process for the operator. In an embodiment implemented using a mobile phone the custom loader was created as an Android-based custom loader, which locks down the phone so that the phone is automatically in this application. All other device functions will remain inaccessible. The operator and user cannot access the homescreen or exit the application. This was performed by setting device owner mode during set-up of the device with the following command prompt:

adb shell dpm set-device-owner
com.smileyscope.smileyscopelauncher/.DeviceAdminReceiver Alternatively, a multi device management system allowing lock down of phones or other devices in accordance with specified use limitations may be used as alternative to a custom loader. The lock down specifications can define the limitations for running the VR experience and locking functionality for the headset.

Optionally the device can also be configured to automatically load the last used VR experience procedure. This feature may be desirable in an environment where the device will be used serially for a number of patients undergoing the same procedure, for example an immunisation clinic, or blood bank. An embodiment configured for automatic recall/start of a VR experience that was previously selected is implemented by persistence of the last selected experience. In this embodiment this value was set by the native Android UI configuration screen and read by the Unity experience.

Figure 5A:
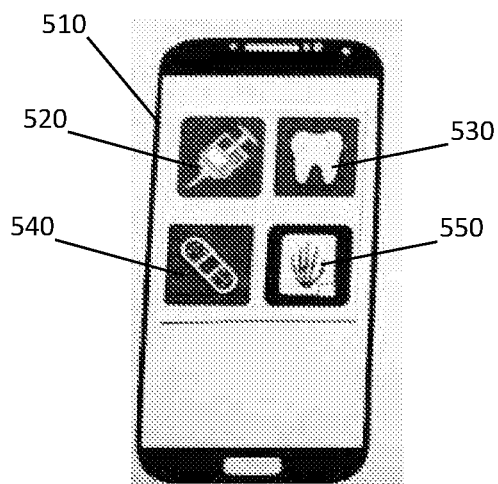
FIG. 5a shows an example of procedure icons.

Alternatively, the device may provide a home screen showing icons or a list of procedures for easy selection of an appropriate VR experience via a touchscreen interface or hardware buttons. FIG. 5a shows an example of procedure icons. Other features for control of the VR experience may also be accessed via the touchscreen and/or buttons. This feature of providing a user interface "outside" the VR experience is a modification to current VR devices. This feature enables the operator to select and control the VR without needing to wear the headset.

Figure 5B:
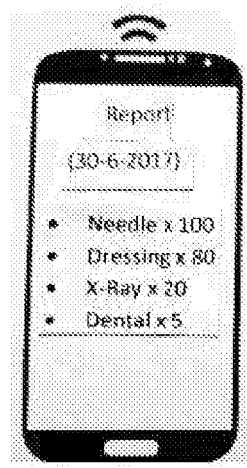
FIG. 5b shows an example of a report of device usage.
Figure 5C:
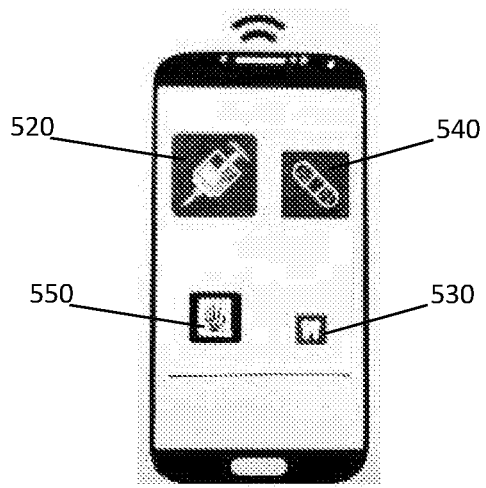
FIG. 5c shows an example of procedure icons.

In an embodiment the device can be configured to automatically tailor icons to the specific device through use of artificial intelligence algorithms. In this embodiment usage data is collected (for example, via Google Analytics) and is fed into the AI algorithm to tailor the presentation of icons to bring to the fore icons more commonly used. An example of an embodiment is illustrated in FIGS. 5a to 5c. Initially the VR device is preloaded with a range of VR experiences. FIG. 5a shows a set of icons identifying the set of procedures for which the VR device 510 is loaded with VR experiences, for example needle 520, dental 530, dressing 540 and X-ray 550. The device is configured to monitor the device 510 usage. Each time a VR experience is used, data is captured for analysis. This data can be transmitted to an analysis engine and analysed. For example, FIG. 5b shows an example of a usage report. For example, this may be an emergency department usage report, showing that needle procedures are the most commonly used, followed by dressing procedures. Usage reports maybe transmitted periodically (for example: daily, weekly, hourly etc.)

alternatively usage data may be sent after each use or after a number of uses. Usage data reports can include use timing data, i.e. time of experience start, duration. The analysis includes running through an artificial intelligence (AI) algorithm. In an alternative embodiment an analysis engine may be implemented on board the device. The output of the usage analysis can be used to tailor the layout of VR icons. For example, icons for more commonly used VR experiences may be positioned toward the top of the screen. The AI algorithm provides updates back to each specific VR device which tailor the icons according to frequency of use. In an embodiment, icons for more used procedures can be emphasised by moving these to a more prominent position on the display. The size of icon may also be modified. For example:
a. Larger and positioned higher up on the touchscreen menu if that VR experience is used more frequently;
b. Smaller and positioned lower down on the touchscreen menu if that VR experience is used less frequently.

For example, as shown in FIG. 5c, the VR device 510 used in this Emergency Department will have tailored icons with larger needle 510 and dressing 530 icons than the fracture/X-ray 550 and dental 520 icons. Further the position of the dental 520 icon is moved to downward on the screen and the more used dressing 540 icon moved to a more prominent upper position on the screen.

This tailoring can be specific to each device to enable icons to reflect the changes in activity over time. Some embodiments can also be able to predict patterns of usage including specific times of day and sessions where specific VR experiences are most likely to be used.

Figure 6:
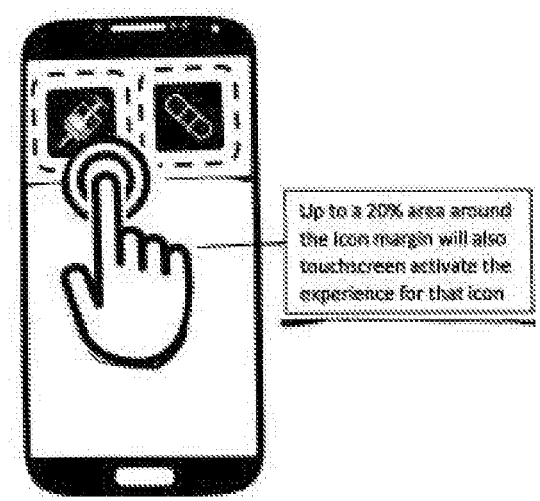
FIG. 6 illustrates an increased margin of error around the touchscreen icons for selecting the icons.

An embodiment can be configured such that a broader area around icon may activate the icon. The touchscreen and icon layout of this embodiment is designed to allow for <20% area around the icon to also activate the icon. This enables the icon to be selected easily with a reasonable margin of touchscreen error. FIG. 6 illustrates an increased margin of error around the touchscreen icons for selecting the icons. This feature can be desirable for busy environments where a practitioner may not be able to fully focus concentration on the touchscreen or need to move quickly, such as a busy emergency room.

Embodiments may also enable voice activated selection of VR experience: the app can be programmed to detect voice activation of specific sub-applications that could be selected. For example, if the clinician verbalises "venepuncture" the app will select the venepuncture VR experience.

Figure 7:
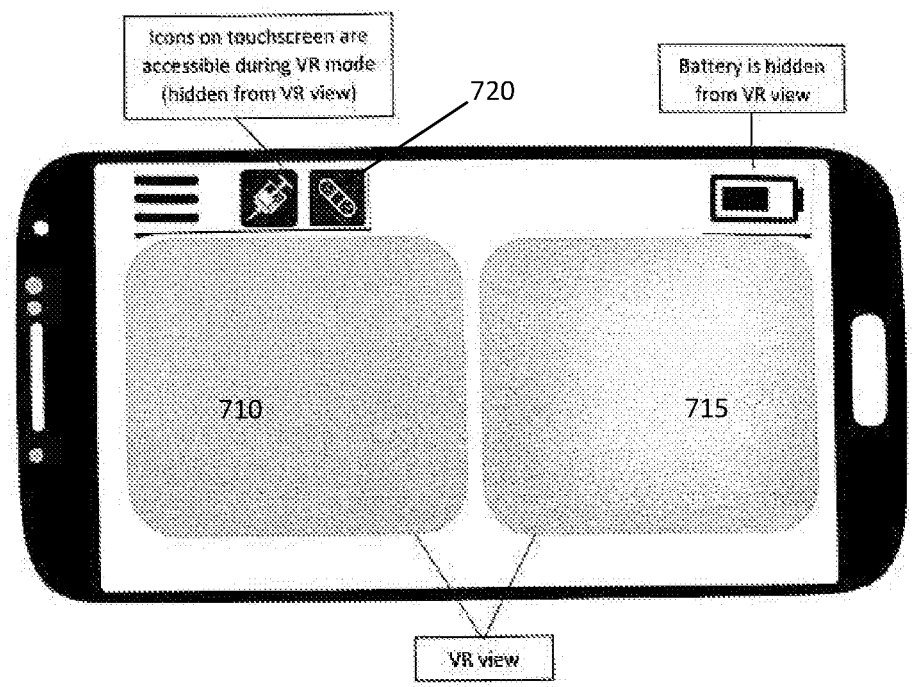
FIG. 7 illustrates a dual interface having a VR mode and touchscreen menu accessible on the same screen.

In an embodiment the device can be configured to provide a dual interface having the VR mode and touchscreen menu accessible on the same screen, but with the touchscreen menu hidden from VR view. For example, as shown in FIG. 7 the display displays stereoscopic VR view images 710, 715 and a user interface 720 in a region above the stereoscopic display windows 710, 715, that will be hidden from the user's view by the headset. To implement this embodiment buttons were overlaid to provide a user interface accessible by the operator on parts of the screen hidden while in VR view. The headset may be configured to allow this UI to be accessed by the operator while the user is engaged with the VR experience. An embodiment of the user interface as built using native Android libraries, by wrapping the Unity context with a custom activity.

The VR device can be configured to go into idle mode after specific period of time: to conserve battery through a combination of gyroscope and time. The VR experience only plays if use is detected. If not in use, the device returns to idle screen to save power. Embodiments programmatically disable the screen and pause the experience when the gyroscope is detected to be still for a defined period, for example 10 to 30 seconds. The system assesses the gyroscope to be still if it has an angle delta less than 1 arc degree for a given update frame. The assessment as still triggers an activity which blacks out the screen and dulls the device back light. The activity polls the gyroscope at a low interval to detect significant motion. On significant motion, the activity removes itself, and resumes the experience. Alternatives could include other sensors (sound, light, positioning).

Embodiments of the VR devices are configured for pre-loading the rendering of the VR experiences. This can optimise the VR experience through enabling higher frames per second (FPS).

Figure 8:
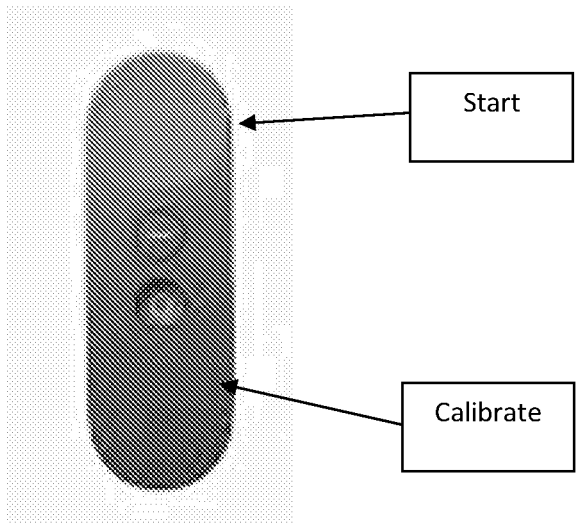
FIG. 8 is an image of an external controller device of a prior art VR device.

A significant modification in embodiments of the VR device is providing calibration and VR experience start in one function. This enables the experience to start and calibrate seamlessly without needing the operator to wear the headset to start the experience. The sequence could be activated from buttons on the phone, headset or external controller/device. Alternatively, the VR experience may be stated from a computer. An embodiment implemented using a mobile phone provides a calibration user experience flow, using the devices volume buttons. For example, when a nurse places the headset on a patient, they tap the volume buttons three times in quick succession to restart the experience. From any point in the experience, in response to this input the device is configured to recalibrate the horizontal centre of the headset, and restart the experience. This is significantly different from prior art in a number of ways:
a. No other known commercially available VR device has the combined function of calibrate (orient direction, focus) and start the experience.
b. Google Pixel/Daydream (closest known VR device before the priority date of this application) requires the end-user to wear the VR headset and press the external controller (depicted in FIG. 8). The direction the controller is pointing will dictate the direction of calibration. The experience icon must be visualised in VR and the 'start' button pressed on the external controller to start the experience. The prior art is not appropriate for use in a clinical context because:
   i. The external controller would be lost easily in busy clinical environments.
   ii. The operator would need to wear the VR headset to start the experience.
   iii. The operator cannot replay the experience without using the external controller—this means that if they are engaged in a procedure they would need to remove their gloves and put on the VR headset to replay the experience.
c. Samsung VR (commercially available VR device) requires the end-user to wear the VR headset and press a button located on the right bottom surface of the VR headset to calibrate and start the experience. This device is also not appropriate for clinical environment use as the operator would need to put on the VR headset to select and start the experience, and then transfer the headset to the end-user.

The calibration and start sequence is specifically designed to ensure that it is easy activated by the operator, but not the end-user. Other functions, buttons and sequences are locked down so they cannot inadvertently pause/re-start/exit the experience.

Figure 9:
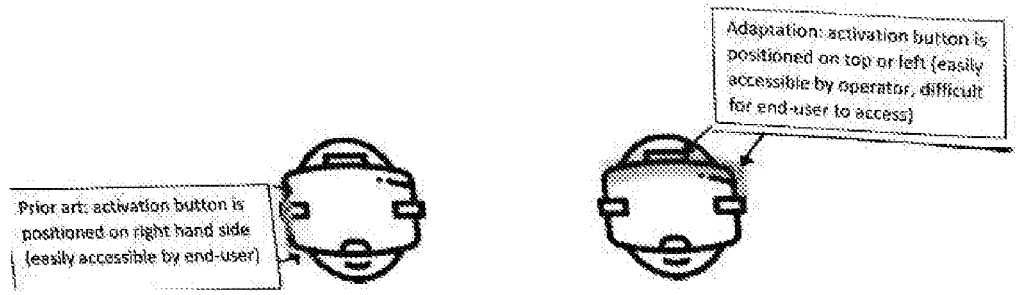
FIG. 9 illustrates positions of control buttons on prior art VR devices and an embodiment of the present invention.

In embodiments of the VR device the sequence activation button has been positioned to ensure it is physically easily accessed by the operator but not the end-user. For example, in the prototype mobile phone embodiment the sequence we selected was tapping the volume button which is the top-centre position of the headset. Currently known commercially available VR devices have the activation buttons on the right-hand side (lower surface e.g. Samsung Gear, or lateral side surface e.g. Google Cardboard). Some commercially available VR devices and also use external controllers, in a clinical setting an external controller may be undesirable as this may be easily misplaced. For the prototype embodiment of the inventor's VR device the top-centre position was chosen, but the physical positioning of the button could be any position on the top of the VR device or left-lateral side. FIG. 9 illustrates the activation buttons are positioned top/left on the VR device to improve operator access.

Embodiments may also be configured to enable external observation of the VR experience, for example for a parent or clinician to observe what the patient is experiencing in the virtual world. For example, in an embodiment the VR device may include an additional screen on the side or front of the device which shows a 2D (i.e. one eye) rendering of the VR experience. In an alternative embodiment the VR device may be configured to pair (i.e. via Bluetooth or WIFI) with another device—such as a parent phone, tablet, smart watch etc. to enable third party observation.

Embodiments may also be configured to capture patient biological feedback data which may be utilised to dynamically modify VR experiences, for example to repeat relaxation exercises until a patient heart or respiratory rate are within a target range to move on to the next step of a procedure, or provide instructions or incentives through the VR experience for the patient to stay still. In some embodiments, biofeedback data may be monitored via the VR device, for example eye movement tracking, pupil dilation, vocalisations which may be captured using device cameras and microphones. Devices may be also be provided with sensors for monitoring patient temperature, respiration, oxygen saturation, heart rate etc. Alternatively, such patient biofeedback may be monitored using conventional equipment and biofeedback data being transmitted to the VR device. Dynamic modification of VR experiences is discussed in more detail below.

VR Experience Framework

An important aspect of the present invention is the characteristics of the VR experiences and specificity of each experience to a physical procedure. Each VR experience is designed to provide a narrative coordinated with the steps of the physical procedure to facilitate re-imagining of the physical procedure experience by the user. The choreography between VR and physical procedure is important to enable reframing of physical sensations—preferably for perception as less painful or intimidating—in the context of the VR experience. VR experiences are created aiming to reframe physical sensations to transpose perception of the physical sensation to something less painful or intimidating for the patient.

Figure 10:
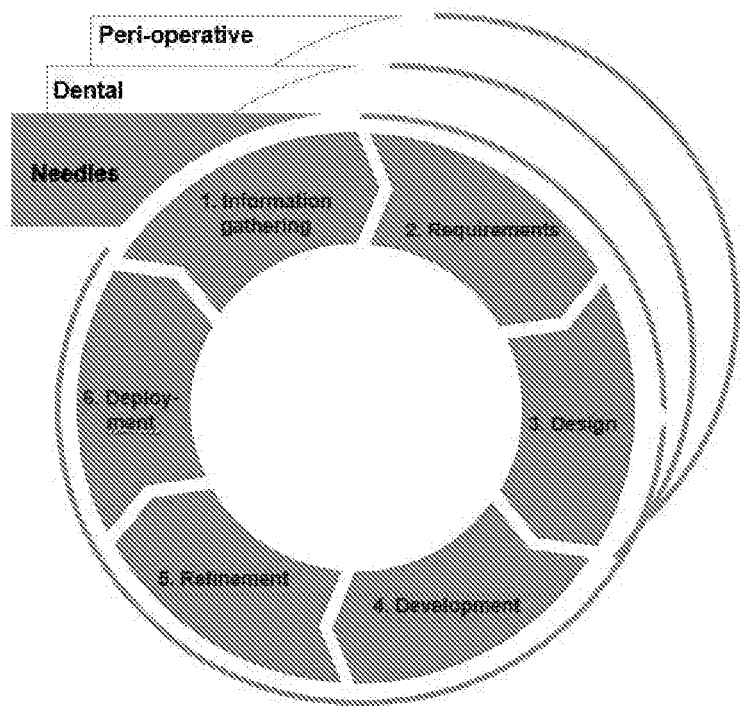
FIG. 10 provides an overview of the framework used by the inventors to create the VR procedure-specific experiences to optimise procedural outcomes.

FIG. 10 demonstrates the development process the inventors undertook to develop the methodologies to prepare the scenes and stories. This process provides an outline of the methodology being used by the inventors to develop the procedure specific VR experiences.

1. Information Gathering
    The inventors reviewed scientific literature and existing studies in the clinical area of interest. Examining best practice techniques in digital and paediatrics, pain management through discussions with domain experts, written and electronic materials.
    The inventors performed surveys and initial VR user tests identify their key concerns around healthcare procedures, previous healthcare experiences, and also interests and hobbies of prospective users—for example children. The inventors confirmed that needle procedures were the most feared part of a child's healthcare experience, and one of the most common causes of pain in healthcare settings.

2. Requirements:
    From the information gathering findings, the inventors identified and specified requirements for the VR experience.
    These requirements were prioritised into groups: critical, important, desirable, exclude.
    The landscape was scoped to evaluate existing off-the-shelf products. The inventors found that there was no appropriate VR experience that was suitable for needle procedures. Although VR has been used to distract children during needle procedures, it was not known to combine multiple techniques into a timed VR experience for the procedure.

3. Design:
    Storyboard and wireframes are designed: multiple medical procedures are observed and timed, to identify activities within the procedure and specific time-points for each of these activities. This storyboarding is used to choreograph the VR experience with the procedure. A storyboard is designed to reflect the specific timing and activities that occur during these time-points. Requirements for the operator (clinician/operator) and (patient) for each activity are fed into the storyboard development.
    Significant input needs to be provided by paediatric healthcare practitioners, developers and designers to iterate on the storyboard and wireframes. Of particular importance for the storyboard is characterising the physical sensation anticipated during steps of the procedure, and the desired perception transposition for each sensation which, in turn, guides selection of creative elements of the VR experience narrative. For example, FIG. 13 illustrates examples of physical procedures and the physiological pain level and intensity typically anticipated for these procedures. It should be noted that different procedures, for example a needle prick compared with a wipe can have differing levels of pain and intensity. These can vary depending on physical aspects of the procedure (for example, size of needle, wipe over an open or closed wound etc.) The actual physical nature of the procedure cannot be changed, what the aim of the VR experience is to transpose the perception of the physical sensation into something less threatening and/or which may be understood by the patient to cause a sensation similar to that caused by the physical procedure but associated with less pain or is pleasant (even if somewhat painful such as a prick from a pinecone or rough lick from a cat's tongue) so that due to immersion in the VR experience the patient perception is transposed to that of the more pleasant experience. FIG. 13 illustrates that different creative scenarios may characterise the physical sensation in an alternative way and therefore be applied for reframing each sensation in a VR experience.
    Prototypes to be designed based on the storyboard and pressure-tested 4. Development:
    In this phase prototypes VR experiences are developed and tested.
    a prototype VR experience was developed using Unity (C#) and multiple builds created 5. Refinement and user testing
    In this phase user testing is performed (for example over 100 user tests) to understand their VR experiences from operator (clinicians) and end-user (patients, families) perspectives.

Figure 11:
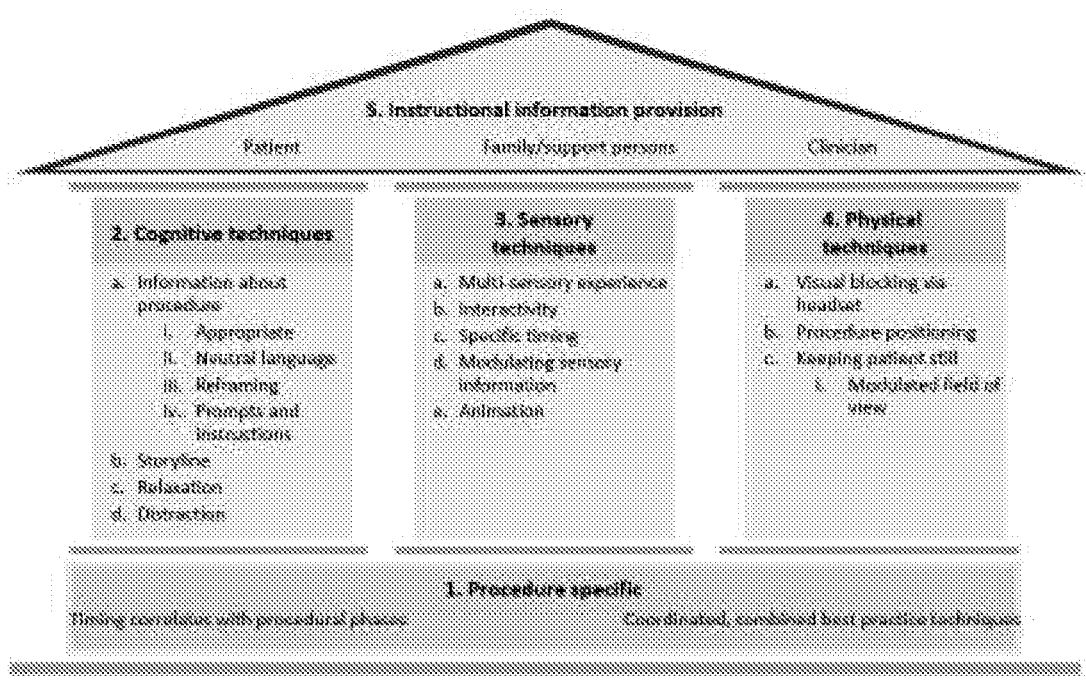
FIG. 11 illustrates a framework of the core techniques involved in the development of a VR procedure-specific experience.

Important aspects of user feedback include:
Storyline
Timing: to ensure it accurately reflected the processes and stages of each procedure (e.g. immunisation, fingerprick test, venepuncture, intravenous cannula). Timing can be refined and re-tested.
Visual and soundscape development
Quality assurance testing, technical optimisation
6. Deployment/implementation, integration
Deployed of the VR experiences to hospitals and clinics, first through clinical trials
There will be potential software alterations during the clinical trial
This phase can also include collection and analysis of data from the trial and usage which may also refine the VR device and VR experiences From the investigative research performed by the inventors they identified core requirements for procedure specific VR experiences and for re-characterising the procedure in a VR experience. FIG. 11 illustrates a framework of the core techniques involved in the development of a VR procedure-specific experience.

The framework is made of five core components:
1. Procedure specific: including procedure phases, and defining timing and activities for specific to the procedure for each phase.
2. Cognitive techniques for providing and contextualising information within the VR scenario.
3. Sensory techniques for modulating perception of sensory stimulation from the procedure
4. Physical aspects
5. Instructional information and support for the patient, family or support persons and clinicians.

The procedure specific aspects are related to the physical steps and actions required for the procedure. However, for many procedures general procedure phases are consistent with those illustrated in FIG. 12, comprising an initial introduction and orientation phase to provide procedural information, calibrates and start the VR experience, information for the procedure may also be provided within the VR context. Typically, a relaxation phase will be used, aiming to prepare the patient for the critical activities for the procedure, instructions for relaxation techniques such as deep breathing can be provided via the VR experience. Aspects of the VR experience such as animations and sounds can also be utilised for relaxation. During this phase the patent may also be prepared for the procedure and both instructed actions and sensations for this process be contextualised in the VR experience. The next phase is the procedure critical point (or points) where the primary procedural action takes place (i.e. giving an injection, inserting a needle, dental drilling, setting bones, cleaning or irrigating wounds etc.) and the characteristics of the VR experience during this phase are to instruct the patient as required by the practitioner (i.e. to stay still, take a deep breath) and to reframe the sensation from the clinical action in a positive context in the VR experience, aiming to alter the patients perception of the sensation into a non-threatening or positive experience. The next phase accommodates remaining procedural actions, again facilitating re-imagining of sensations in the context of the VR experience. A final relaxation phase concludes the procedure. Within each of these phases combinations of cognitive, sensory and physical techniques may be used in the VR experience to enable reimagining of the procedure.

Figure 14A:
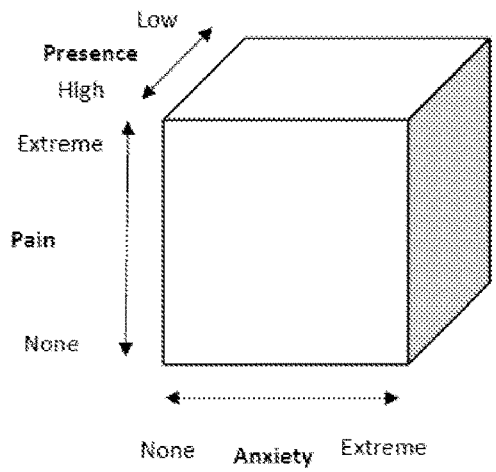
FIG. 14a illustrates a model of pain and anxiety responses for each procedure and requirements for cognitive presence or response from the patient during the procedure.
Figure 14B:
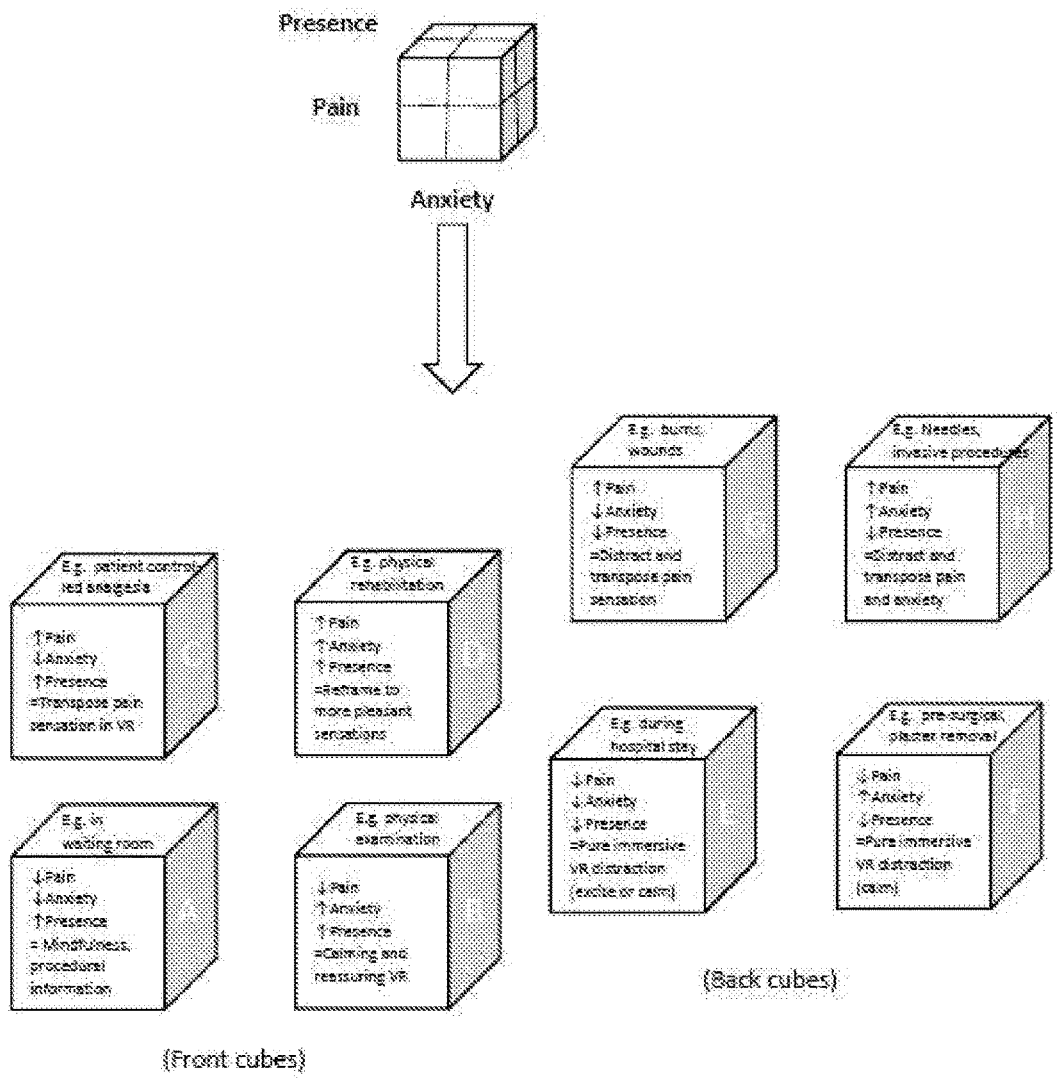
FIG. 14b illustrates sectors of a simplified block model of FIG. 14a and types of procedures for which patient response may be considered characteristic for each sector.

A key aspect of the VR experience is to reframe perceptions associated with the procedure. Therefore for an initial step it is important to understand the anticipated patient response associated with a procedure, for example anticipated pain and anxiety responses and desired transposition through VR to target response perceptions. FIGS. 14a and 14b illustrate a model of pain and anxiety responses for each procedure and requirements for cognitive presence or response from the patient during the procedure. This model is used to develop a resource library of transposition VR or AR experiences for each procedure. The models may vary based on patient age and/or mental acuity.

For ease of reference the current description uses established VR continuum terminology wherein "real environment" refers to completely real world objects and interactions, "augmented reality (AR)" refers to adding computer generated content to the real world, "augmented virtuality (AV)" refers to adding real world information to a computer generated environment, and "virtual reality (VR)" completely computer generated environment. AR and AV can also be referred to under the umbrella term of "mixed reality".

The overarching framework used to determine the most appropriate way to support patients during procedures is determine by 3 continuums: 1. Level of pain caused by the medical procedure; 2. Level of baseline anxiety of the patient/client; 3. Level of presence either required by the procedure (e.g. need to be present and aware as the patient is required to follow specific commands or actions) or preferred by the patient/client (e.g. a patient personally prefers to be fully aware of the procedural steps versus being very distracted), FIG. 14a illustrates these three continuums as axes for a 3D block model although this may be equally conceptualised as a spectrum. Depending on where the patient undergoing the procedure lies on these spectrums determines the VR approach. To illustrate some scenarios, in FIG. 14b each spectrum is divided into 'low' and 'high' (artificially to keep it simple, although in reality this would be a continuum). FIG. 14b illustrates sectors of this simplified block model and types of procedures for which patient response may be considered characteristic for each sector.

Therapeutic VR transposition approaches will vary depending on the baseline patient and procedural requirements. Some examples of the common scenarios where this may be applicable include but are not limited to:
Block B (low pain, high anxiety, high level of presence and cooperation required): E.g. a patient is required to cooperate with a physical examination and thus be present and able to take instructions from the clinician, and potentially interact with real objects in the room, e.g. standing on some weighing scales, pushing against a real object for muscle strength. AR medium: will be calming and reassuring, provide information and explain what the patient (e.g. child) is required to do.
Block D (high pain, high anxiety, high level of presence and cooperation required): E.g. a patient requires physical rehabilitation post-operatively. It may be painful and anxiety-provoking, however the patient is also required to be present in the physical world and cooperate with the different exercises. AR/VR medium: will actively reframe the pain sensations in a more positive way, but also make the rehabilitation exercises fun. For example, this may be gamified with visual prompts on progress and reward systems.
Block H (high pain, high anxiety, low level of presence required): E.g. a patient may be undergoing an invasive medical procedure such as a needle insertion or wound dressings changes. VR: will enable the patient to virtually escape the procedure room, be distracted and transpose the pain into a more positive sensation.

In regard to VR, there are different senses which can be manipulated and transposed to improve the patient's perceptions of pain and anxiety. Some examples include:

Physical sensations (e.g. fingerprick needle transposed to playing with pine cone, cleaning a wound transposed to cat licking you).

Sights (e.g. a needle drawing blood transposed to a fish having a quick nibble).

Sounds (e.g. popping noise of a J-tip local anaesthetic syringe transposed to splashing water, MRI scanner noise transposed to boat chugging along).

Smells (e.g. cauterisation transposed to burning scraps on a campfire, antiseptic wash transposed to a mop bucket or smells of forest sap).

A medical procedure can feel disempowering and stress-provoking for the patient and family. The inventors recognised that they can strengthen a child's ability to cope well with medical procedures through supporting them through the entire end-to-end procedural journey. This includes preparing families for the procedure through education and simulation, transposing painful sensations into more positive ones, and debriefing and providing feedback post-procedure. This phase may also include proceduralist preparation and optionally training for the proceduralist to ensure they can provide the best experience possible form the integration of procedure, VR experience and, only if necessary, additional pharmaceutical pain management or sedation. A general overview of the end to end framework is shown in FIG. 15. The first phase is an education phase, which enables the child and family to understand: the rationale for the procedure; what to expect; what they need to do; and to try VR. This first phase may use conventional 2D media or VR or a combination of both. The second phase is an observation phase to enable the child and family to: select a character; and watch what will happen to that character undergoing the procedure. This phase may use conventional 2D media or VR or a combination of both. The third phase is a practice phase to enable the child to: acclimatise to the procedure room; play and explore the area; simulate the procedure; and practice with elements adjusted as required (e.g. sound volume). The parent or clinician may be able to modify elements of the procedure and/or VR experience during this phase for example choosing different VR scenarios for use in the procedure. This phase may use conventional 2D media, AR or VR or combinations. Data regarding the patient response to the simulation may be captured during this phase. The fourth phase is an assessment phase which enables the child to undergo a mock procedure to assess their needs: simulates procedure; and monitors response and ability to comply with the procedure. This phase may use conventional 2D media, AR or VR or combinations. Data regarding the patient response to the simulation may be captured during this phase, for example this may be done automatically via the VR device or other devices used during the simulation. The clinician may be able to make modifications if required for the patient during this phase. The fifth phase is a clinical review which enables clinician to review patient's response in simulated environment: assess suitability for the procedure; plan the strategy and approach best suited to the child's needs. This phase may use conventional 2D media, AR or VR or combinations. The sixth phase is a preparation phase which prepares the child and family for the procedure: supports pre-procedural anxiety; reminds the child and family about important aspects of the procedure; and distracts child while waiting. This phase may use conventional 2D media, AR or VR or combinations. The seventh phase is the procedure phase where the VR or AR is used during the procedure to Supports the child during the procedure: distract; reframe or transpose perceptions; reduce pain, anxiety, distress; and increase cooperation. During this phase the VR or AR can modulate the patient perception of the procedure. The final phase is an evaluation phase where all participants are able to provide feedback on the experience: assess what worked and what could be improved; clarify preferences; and determine future needs. It should be appreciated that the patient may be required to undergo multiple procedures, or repeat procedures (for example chemotherapy or dialysis patients) so the evaluation phase may form part of a feedback loop for ongoing treatment and continual tailoring of VR experience to improve the outcomes for the individual patient.

A specific example of an end to end framework applied for an MRI procedure is illustrated in FIG. 16. In this example the education phase enables the child and family to understand: why the child is getting an MRI; what the MRI scan will involve, including a needle to inject contrast; and they will need to stay still in the MRI scanner for 20 minutes. The child can then select a character to watch go through the MRI procedure, before proceeding to the practice phase where the child can undergo section of or the whole MRI procedure through a VR experience. This enables the child to practice at home: to acclimatise to the MRI room; explore the MRI room; simulate the procedure; and practice with softer MRI sounds, which gradually become louder if the child is tolerating the simulation. The assessment phase enables the child to undergo a mock procedure in VR to assess their needs: simulate the needle procedure, IV contrast injection and MRI scan. The VR or other equipment can be used (optionally in conjunction with clinician observations) to monitor response, and sensors assess whether the child could comply with procedure—in particular the requirement to remain still for the MRI scan. The review phase enables the clinician to review the patient's response to the simulation: assess the child's ability to stay still for the sufficient scanning period and plan the approach—e.g. awake scan or sedation level required. In preparation for the procedure VR in the waiting room prepares the child and family for the intravenous needle for contrast: supports pre-procedural anxiety; enables insertion of the intravenous needle—for example minimizing pain and anxiety; distracts child while waiting. Where VR can be used in the MRI room this supports the child during the MRI scan: distract; reframe or transpose perceptions such as the loud noises; reduce pain, anxiety, distress; increase cooperation and staying still during the scan. An MRI compatible VR headset is required in the MRI room to avoid interference with the MRI. However, preparation phases outside the MRI room may involve VR. In cases where full visual VR cannot be used in the MRI room, through imaginative training and VR experience of the MRI environment and maybe auditory VR and/or visual images projected into the room or visible on screen form the room, a child may still imagine a VR scenario and have increased compliance with the procedure with reduced requirements for sedation or other intervention.

Post procedure the child and family report what worked well, could be improved, and preferences for future procedures. The clinician typically records the approach used (e.g. light sedation, reduced sound, calming VR) and any modifications recommended for future procedures.

Figure 17:
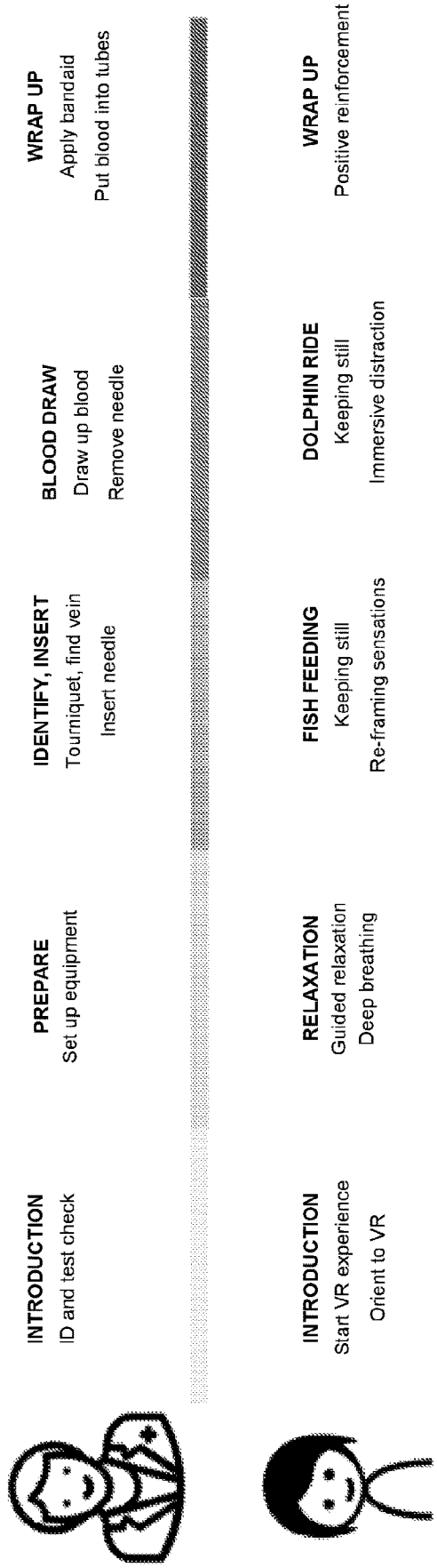
FIG. 17 shows an example of reframing a needle procedure using VR.

This end-to-end journey is the framework that the inventors have developed, which guides an approach to developing a series of VR experiences that improve patient outcomes. The VR experience for the procedure reflects the real-world experience, and the VR experience is coordinated and timed to the real-world experience. An example of how this is mirrored in our needle procedure for children, to reframe experiences is outlined in FIG. 17. This example mirrors the real-world experience (taking bloods) with the child's VR experience (underwater example). Each sensation of the real experience has a corresponding experience in the virtual world. The real life and VR are choreographed so that the patient experience is that of the VR world, with the physical sensations perceived as the transposed VR experience. The idea being that the modulation of perception means reduced pain and anxiety for the procedure.

The VR experiences can be designed and created from a VR resource library, which enables you to customise the VR experience based on the procedure, therapeutic intent, and individual end-user preferences. These components form the foundations of the therapeutic VR experiences. Some VR experiences are already pre-programmed for specific procedures and purposes, but can be customised for individual users. Others can be created from scratch according to the needs of the individual and procedure required. It should be appreciated that although we refer to VR experiences, these may be experiences on a VR continuum, including mixed reality/AR allowing some real world perception and interaction well as total immersion VR.

FIG. 18 conceptualises the clinician controlled/variable aspects procedures and VR experiences, these being related substantially to the requirements of the procedure and desired outcomes from the VR (for example, patient compliance during the procedure, pain management). The patient variable/controllable aspects relate to guiding selection of perception modulation strategies for building a patient and procedure specific VR (or AR) experience. The VR experiences can be designed and created from a VR resource library, which enables customisation the VR experience based on the procedure, therapeutic intent, and individual end-user preferences. These components form the foundations of the therapeutic VR experiences. Some VR experiences can be already pre-programmed for specific procedures and purposes, but can be customised for individual users. Others can be created from scratch according to the needs of the individual and procedure required.

To provide more detail about the resource library, one very important component is the way in which real-world procedural elements are transposed into the virtual world, in such a way to be less threatening and more positive than in reality. The transposition may completely replace the real life sensation (e.g. virtual reality world completely blocking out and replacing the view of the real world), or augmented, where the real world can still be experienced but specific elements are "augmented" by computer-generated perceptual information (e.g. sounds or smells are made more positive by a complementary sensation that enhances positive perceptions).

The aspects of the framework for developing VR experiences will now be discussed in more detail.

Figure 12:
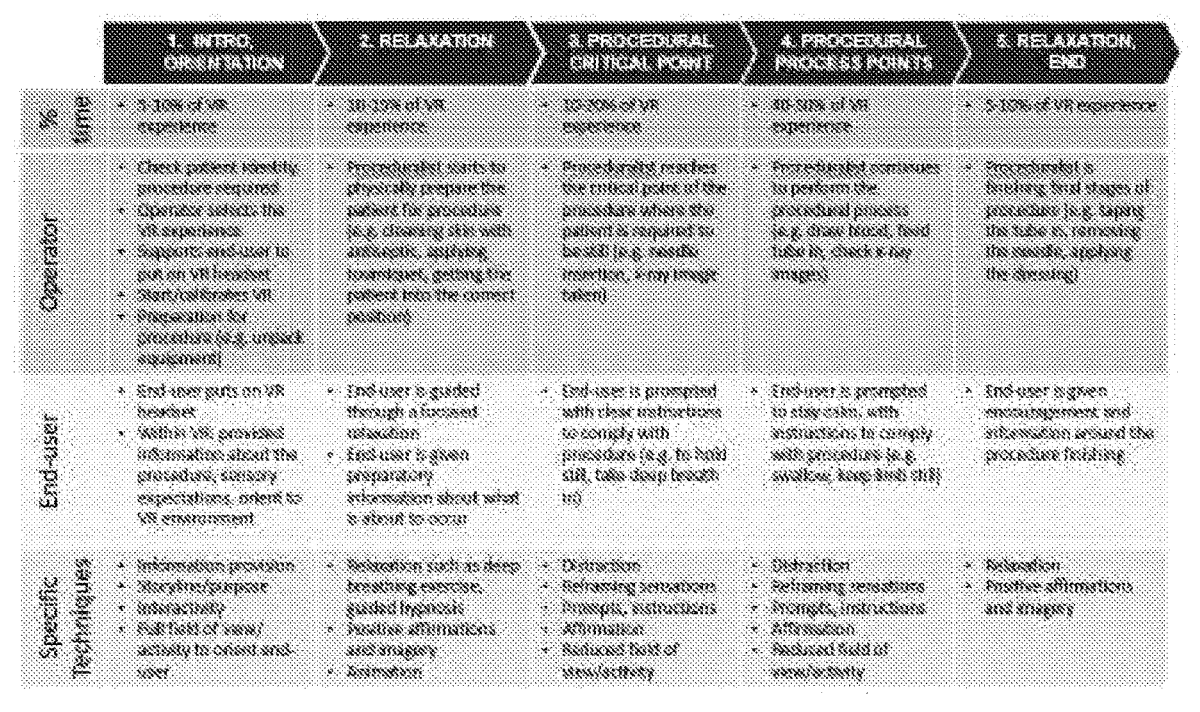

1. Procedure-specific: the VR experiences are focused and customised to one specific procedure (or group of related procedures). This principle allows the VR experience to be optimised and targeted towards the procedure. For example, the inventors have developed a prototype series of three VR experiences for needle procedures. These experiences are timed specifically to the procedure as a whole, and reflect different procedural phases. For example, venepuncture (needle to draw blood from the vein) takes an average of 3-5 minutes from set-up to securing the final dressing. The VR experience for venepunctures is customised to last the entire procedure (3-5 minutes) and the storyline is developed to reflect the specific procedural phases. The procedure time may vary and VR experiences of different lengths be generated accordingly, for example 1 minute (e.g. for injection), 3 minutes (e.g. for venepuncture), and 7 minutes (e.g. for IV cannulation). Other types of procedures are also envisaged which may have different duration or number of steps.
   a. We have classified needle procedures into five phases which require specific activities from the operator and end-user. These are illustrated in FIG. 12, with indicative timeframes and techniques for each phase.
   b. Timing of the VR experience is in part controlled by the end-user (e.g. there are a specific number of fish the patient needs to look at/interact with before the VR experience moves to the next phase). There are also time-outs so that if the patient does not complete the interactions/tasks within that time period, the VR experience will automatically move to the next phase.
2. Cognitive techniques: multiple psychological and information-giving techniques are incorporated into the VR experience to empower the patient, and enhance their procedural experience. This includes:
   a. Information about procedure: provided in audio and visual styles. This includes explaining the steps of the procedure, what to expect, and what the patient needs to do at each stage (e.g. extend arms out, hold still, relax muscles). More specifically, the information is:
      i. Appropriate: targeted at a specific audience, age, culture and language
      ii. Neutral: the information about the procedure is deliberately chosen to be non-threatening and factual. For example, using affirmative language (e.g. "we need to put in a straw under the skin to give you some medicine to help your body heal quickly") rather than coercive or negative language (e.g. "you'll stay sick if you don't let me put in this needle"), and avoiding descriptors such as 'sting' or 'hurt'
      iii. Reframing: the information is reframed in VR so the patient can re-imagine the sensory details of the procedure in a more positive way. For example, "You might feel some cool waves washing over your arms" to explain the anaesthetic wash, and "imagine they are just some fish coming into say hello and have a quick nibble" to reframe the needle insertion. This allows patients to anticipate what they will see, smell, hear and feel, but be able to use the VR experience to reframe their sensations
      iv. Prompts and instructions: are provided throughout the VR experience to support the patient, family and clinician, which prepares them for each stage of the procedure. For example, the patient is asked to extend their arms (for a blood test) and keep still (during the needle insertion)
   b. Storyline: each VR experience has a clear storyline and provides purpose for the patient. The narrative and purpose allows the patient to focus on the VR experience rather than the procedure. For example, the patient is briefed at the start of the VR experience "your mission is to find the whale and make sure it is ok".
   c. Relaxation: deep breathing and muscle relaxation prompts are implemented throughout the experience. A relaxation exercise is introduced early in the VR experience to encourage deliberate focus on relaxation, and then prompted during the procedure. This helps reduce patient stress.

d. Distraction: immersive distraction techniques in VR enable the patient to 'escape' the hospital environment temporarily during the procedure and be in an immersive, interactive and pleasant environment.

3. Sensory techniques: VR provides an immersive, multi-sensory experience for patients to be distracted and absorbed within, which in turn allows for a better procedural experience.

a. Multi-sensory experience: incorporates all the senses (sight, hearing, touch, smell, taste) and provides a coherent narrative to their sensory experience. For example, when the needle insertion phase is re-framed as feeding fish, the child sees the fish (which activates the fish to move), hears the fish play musical notes when activated, feels the fish nibble/feed on their arms (i.e. clinician feeling for veins and inserting the needle). If the procedure is also performed under sedation, the smell and taste of the surgical mask and gaseous anaesthetic can be reframed as wearing a 'diving' mask and being encouraged to take deep breaths and blow bubbles. These seemingly creative type aspects of the narrative are carefully selected based on the criteria of:

having an associated physical sensation at least similar to a sensation experienced during the physical procedure encourage the patient to physically respond as required by the operator—for example to stay still, to reposition a limb, to breathe at a required time or rate etc.

non-threatening appropriate within the context of the narrative—to enable the sensation to feel part of the virtual world optionally to be engaging, entertaining, amusing etc.

b. Interactivity: the VR experiences are designed to be interactive in this case visually by looking at objects, but could also be via hand-held sensors or controllers and voice. The interactivity is choice-based, so the objects are deliberately off-centre to enable the patient to choose whether or not they want to interact with the object. This allows patients to feel more empowered and in control of their situation and environment. This can enable some patient control over the pace of the procedure, based on monitoring the interactions within the VR experience, for example by delaying the next phase, and the narrative coordinating the actions of the clinician, until the patient interaction is complete indicating readiness for the next phase. Readiness for a next phase may also be gauged by the VR device based on physiologic feedback from sensors i.e. heart rate, respiratory rate, pupil dilation, blood oxygenation etc.

c. Specific timing of sensory information is designed to reflect what is happening in the procedure. (See FIG. 12)

d. Modulating sensory information: the amount of sensory information can be controlled (increased/decreased) by the operator (e.g. clinician) or support personnel (e.g. family). For example, if a patient is overwhelmed by the number of objects in their field of view, the number of objects can be decreased. If the patient is bored or requires increased amount of distraction, the amount of sensory information can be increased. This modulation can be triggered by voice, sensor, activation, input, or detected changes in physiological symptoms.

e. Animation techniques have been incorporated to help patients feel safe and oriented within VR. For example, the boat that you dive from at the start of the VR experience remains in view when the end-user is underwater to reassure and orient them within VR. Similarly, the objects do not approach the child directly, but at a non-threatening path.

4. Physical techniques:

a. Visual blocking via headset: the patient does not see the procedure taking place (e.g. needle, missed attempts, blood), through physical visual blocking by wearing the headset. This is preferred in many patients, however there is a significant minority who would like to watch parts of the procedure. These patients are able to see their virtual arms within the VR experience, and fish interactions. This could be alternatively Augmented Reality with patients seeing their real arms, but having fish overlaid on top replacing the patient's view of the clinician inserting the needle.

b. Procedure positioning: positioning prompts encourage patients to take on specific positions during the procedure. For example, the patient is asked to extend their arms (which is reflected in the avatar arms), and face a specific direction (e.g. to have a ride the dolphin)

c. Keeping the patient still: this is an important feature of our VR experiences, which encourages predictable physical movements by the patient, to facilitate the clinician's ability to successfully perform the procedure. For example, this is encouraged through i. Modulated field of view: the amount of visual activity is limited to a 70-100 degree field of view. The activity within the defined field of view encourages the patient to reduce their upper body movement during times when it is important for the patient to keep still ii. Prompts: when it is particularly critical for the patient to keep still 5. Instructional information provision: the techniques are combined and incorporated to provide instructions and information to the patient, family and clinicians. The instructions help patients understand what is required of them during the procedure, and the information provides context and rationale for the procedure and/or sensory experiences. The instructions and information also demonstrate 'best practice' for clinicians. Clinicians are able to follow the instructions at each phase of the procedure. They will pick up the language and information provision skills through repeated exposure to the VR script.

Choreography between the physical procedure and VR experience stems from the procedural requirements and in particular timing for the procedural steps. This timing may be fixed or responsive to feedback from the patient or clinician—for example, waiting for a patient to be sufficiently relaxed, some steps of a procedure may take longer or shorter depending on the circumstances (i.e. dental drilling or giving blood). Thus, VR experiences are typically structured around procedure steps rather than fixed timing and interaction between clinician and VR experience (for example through narratives or other cues) used to choreograph execution of the procedure with the VR. FIG. 19 shows the steps for three procedures which may benefit from VR (or AR) patient support. The steps for common procedures may be defined in a medical resource library. The examples given are Venepuncture (blood draw), lumbar puncture (spinal fluid draw) and Nitrous gas anaesthetic. For Venepuncture the steps are: 1. Introduction 2. Gather equipment 3. Apply tourniquet 4. Clean skin 5. Insert needle 6.

Draw blood 7. Remove needle 8. Apply bandage. For lumbar puncture the steps are: 1. Introduction 2. Gather equipment 3. Position patient 4. Feel spine 5. Clean skin 6. Insert needle 7. Remove stylet 8. Catch Fluid 9. Remove needle. For Nitrous gas anaesthetic the steps are: 1. Introduction 2. Gather equipment 3. Apply mask to patient 4. Encourage deep breaths 5. Monitor while sedated.

For each step of a medical procedure a VR transposition library may store multiple different VR scenarios that may be used to reframe the physical sensations of the procedure or encourage relaxation and patient compliance. The VR transpositions can be developed based on the model discussed above with reference to FIGS. 13 and 14a-b. The transpositions may also be grouped via creative theme for ease of reference to build VR experiences. FIG. 20 shows an example of the steps of the Nitrous gas anaesthesia procedure and corresponding VR transpositions using two alternative themes a space theme or an underwater theme. For the preparation steps of the procedure during the introduction phase the VR theme context is established, for example on a boat near a tropical island preparing to go diving or on a space ship getting ready for a spacewalk. In each of these scenarios the patient is provides with some distraction and introduced to a mindset of using artificial breathing apparatus, which correlates well with the physical requirement for a mask for delivery of the anaesthetic. As the anaesthetist is preparing their equipment the patient is also preparing to go scuba diving or on a spacewalk. The physical action of putting on the anaesthetic mask is coordinated with putting on a face mask for diving or donning the breathing apparatus for a spacewalk in the VR scenario.

An audible narrative may be used to coordinate the actions of the anaesthetist with the VR experience. Alternatively, the anaesthetist may trigger the action in the VR experience, for example via a button or verbal cue such as "it's time to put your mask/helmet on" and once settled instructing the patient to "take some deep breaths to test your equipment", or this may be part of the VR narrative listened to by the anaesthetist to coordinate the actions. The VR experience then continues with the respective scenario with images of diving on the reef or floating up into space to distract the patient and encourage them to remain calm as the anaesthetic takes effect.

For this simple scenario it should be apparent that many different "creative" scenarios may be utilised in the transposition of sensations or reframing of procedural steps, however the characteristics of the transposition is based on the procedural requirements or response modulation in a desired way in accordance with the model described with reference to FIGS. 14a-b. For example, for the steps of applying a face mask and taking deep breaths to inhale the anaesthetic the anticipated patient response would be one of anxiety rather than pain, but the patient needs to cognitively respond—follow the instruction to take deep breaths—thus the objective for reframing is to reduce anxiety while retaining sufficient cognitive presence to follow instructions reframed in the context of the VR experience. Using the space or underwater scuba diving scenarios provides alignment of the physical sensations and cognitive response to instructions with the procedural requirements, in an entertaining fantasy context. It should be appreciated that for patients with a fear of water a diving scenario may be inappropriate and not server to reduce anxiety, for such patients a space theme may be more appropriate. Other scenarios may also be used, for example smelling perfume samples at a fairy perfume factory, dressing up for a costume party and putting on a mask of a dog's nose and checking you can still breathe properly etc. It should be appreciated that the nature of the creative context of the VR experience is highly variable and many different creative scenarios may be applied for a similarly characterised VR transposition.

For each procedural action characteristics of a VR transposition for modification of perception for the action in at least one of pain, anxiety or presence can be defined. The VR transposition being defined based on the requirements of the procedure for presence and aspects of the action inducing physical sensation, and target direction for modification in one or more of presence, anxiety and pain perception. The transposition being characterised by reframing aspects of the physical interaction in a manner which is not inconsistent with the physical sensation induced by the action and encourages altered perception of the physical sensation. For example, in a VR context transposition actions are characterised as mimicking duration and attributes of the physical sensation (such as pressure, vibration or sharpness) but in a context of an interaction which is typically associated with less pain or anxiety than the actual physical action.

VR transpositions may be designed to alter patient perception but the degree to which that perception is shifted may vary from patient to patient. For example, for one patient reimagining a wipe over a wound being cleaned as a cat's lick may be perceived as rough, but not painful, whereas another patient may still experience some pain response but less than without the transposition. Embodiments of the VR system can use algorithms around pain modulation and grading. Monitoring patient feedback (manual or automatic) can enable a clinician and/or VR system to gauge the extent to which the VR transposition is effective.

A method of generating a virtual reality continuum (VR) experience choreographed to a physical procedure will now be described. The procedure incorporates at least one procedural action associated with a physical sensation and potentially inducing an anxiety or pain response. TO generate a VR experience the order of execution of the procedural actions is determined. For each of the procedural actions characteristics of a VR transposition to modify perception for the action of any one or more of pain, anxiety or presence are then defined. Then for each defined VR transposition a VR experience component fulfils the characteristics of the defined VR transposition is obtained, using a common VR experience theme. Obtaining the VR experience components may involve selecting the VR experience component from a library of pre-prepared VR experience components. For example, the library or database may store a plurality of VR experience components—short VR experience segments which may be joined/edited together to form a longer VR experience—indexed by theme and VR transposition characteristics. The VR experience components can be obtained by look up and selected based on theme and transposition characteristics for physical action. Alternatively, a VR experience component can be created based on the characteristics of the defined VR transposition.

The VR experience components are then compiled into a VR experience based on the order of execution of the procedural actions for the procedure.

An embodiment of the system includes a virtual reality (VR) experience generation system. This system can comprise a medical procedure library, a VR transposition library and a VR experience compiler. The medical procedure library stores one or more sequences of procedural actions for one or more medical procedures. These sequences define the steps required for performing each procedure and may optionally include some timing data such as typical time ranges for execution of the procedural step and/or whether or not the step maybe repeated in a sequence (for example cleaning wound may require multiple swipes depending on the size of the wound. The VR transposition resource library stores for each procedural action associated with a physical sensation and potentially inducing an anxiety or pain response, defined characteristics of a VR transposition to modify perception for the action of any one or more of pain, anxiety or presence. This library also stores a plurality of VR experience components for each defined VR transposition. The VR experience component is a small portion of a VR experience which is directly associated with the physical action and the VR experience component fulfils the characteristics of the defined VR transposition in the context of one or more VR experience themes. For example, a nibble of a fish is a VR experience component associated with an action such as a needle prick, or plucking of a suture—it should be appreciated that the same VR experience component maybe suitable for association with more than one physical action if the VR transposition characterisation is the same for each of the different actions. Each VR experience component is developed in accordance with a theme (for example, scuba diving, fishing, forest, space) to enable VR experiences to be generated using different components selected based on procedural actions but having a common theme so that the individual VR experience components can be compiled in to an end to end VR experience and narrative, ordered based on the procedural steps.

The VR experience compiler is configured to compile a VR experience for a medical procedure by retrieving from the medical procedure library a sequence of procedural actions for the medical procedure. The compiler selects from the VR transposition resource library a VR experience component for each defined VR transposition using a common VR experience theme. Compiling the selected VR experience components into a VR experience is based on the action sequence for the procedure. This may include adding additional VR experience components for linking the action based VR components into a sensible narrative and choreographing the VR experience with the procedure—for example linking VR components may be used (an allowed to be repeated or skipped) to ensure alignment of timing between physical and virtual actions during procedure execution. The VR generation system may be implemented using conventional computer hardware processing a memory resources, such as a PC, server or distributed (cloud) processing a memory resources, with the compiler implemented in software and the databases storing the medical procedure and VR transposition resource libraries. It should be appreciated that the data stored in the VR transposition library comprises VR transposition definitions and VR experience components as discussed above. The VR resource library may also store end to end VR experiences (having one or more themes) for procedures, for example for common procedures, to avoid the need to compile a new VR experience each time the VR experience is required.

It should be appreciated that the VR transformation characteristics are defined based on the physical action, independent of VR theme or creative context. For example, defining attributes of the physical sensation (i.e. duration, intensity, area of the body touched, aspects of any physical device used etc.), requirements for cognitive presence of the patient and desired modulation of the patient response (i.e. reduced pain perception, calming/anxiety reduction). The VR experience components can then be creatively crafted for the VR transposition and it should be appreciated that any number of different creative scenarios may be used.

Embodiments can be configured to enable each VR experience to be automatically modified. Some examples of modifications include:
1. Automatic modification of the experience content and/or clinician user interface (e.g. menu shown or default mode) according to sensor detected anthropomorphic characteristics e.g. head circumference (e.g. impedance plethysmography embedded in headband), vocal pitch (e.g. microphone) as a predictor of age appropriate content
2. Automatic modification of the VR experience (i.e. for needle procedure) as informed by sensor(s) (e.g. camera, voice, worn band or badge, in room sensors operating on light or infrared) to appropriately alter stimuli for example by inserting additional graphical figures to where the operator is or is not, additionally to alter the length of the experience, or play pre or post procedure music
3. Automatic modification of the experience according to the speed at which users interact with the visual stimuli e.g. making fish harder or easier to interact (distance, number, position) with based on time taken to complete of prior school of fish.
4. Automatic modification of the experience based on biofeedback from sensor on the VR device or external sensors/monitoring equipment in communication with the VR device.

Data may be collected during procedures via the VR device and other equipment for use in post procedure analysis—for example for patient reports and research purposes.

Data collected during procedures may also be utilised for modification of VR experiences (either dynamically as the procedure is underway or for future procedures). The data collected depends on the intent and complexity of the procedure or patient's needs. This may include but is not limited to any one or more of:
Physiological observations: heart rate, respiratory rate, oxygen saturation, galvanic skin conductance
Eye tracking, gaze, blink, pupil dilation
Procedure: timing, major movements, key stages, procedural site, procedural success/failure
Voice: to respond to specific voice-activated commands, to identify changes in pitch, volume and rate which may provide indications as to whether the patient is in pain or is overly sedated.

Data can be collected during the VR experience and analysed in order to:
Time and synchronise the VR experience to the real life event (e.g. procedure and proceduralist's actions)
Monitor and accommodate to the needs of the participants (e.g. patient, support personnel)
Assess an end-user or patient's progress
Assess a patient's suitability for a specific procedure and approach (e.g. need for mild sedation or anaesthesia).
Store to provide information on the needs of the patient in future similar procedures (e.g. they had a low pain tolerance last time, so the VR should reflect an increased intensity to match this in future procedures).

Figure 21:
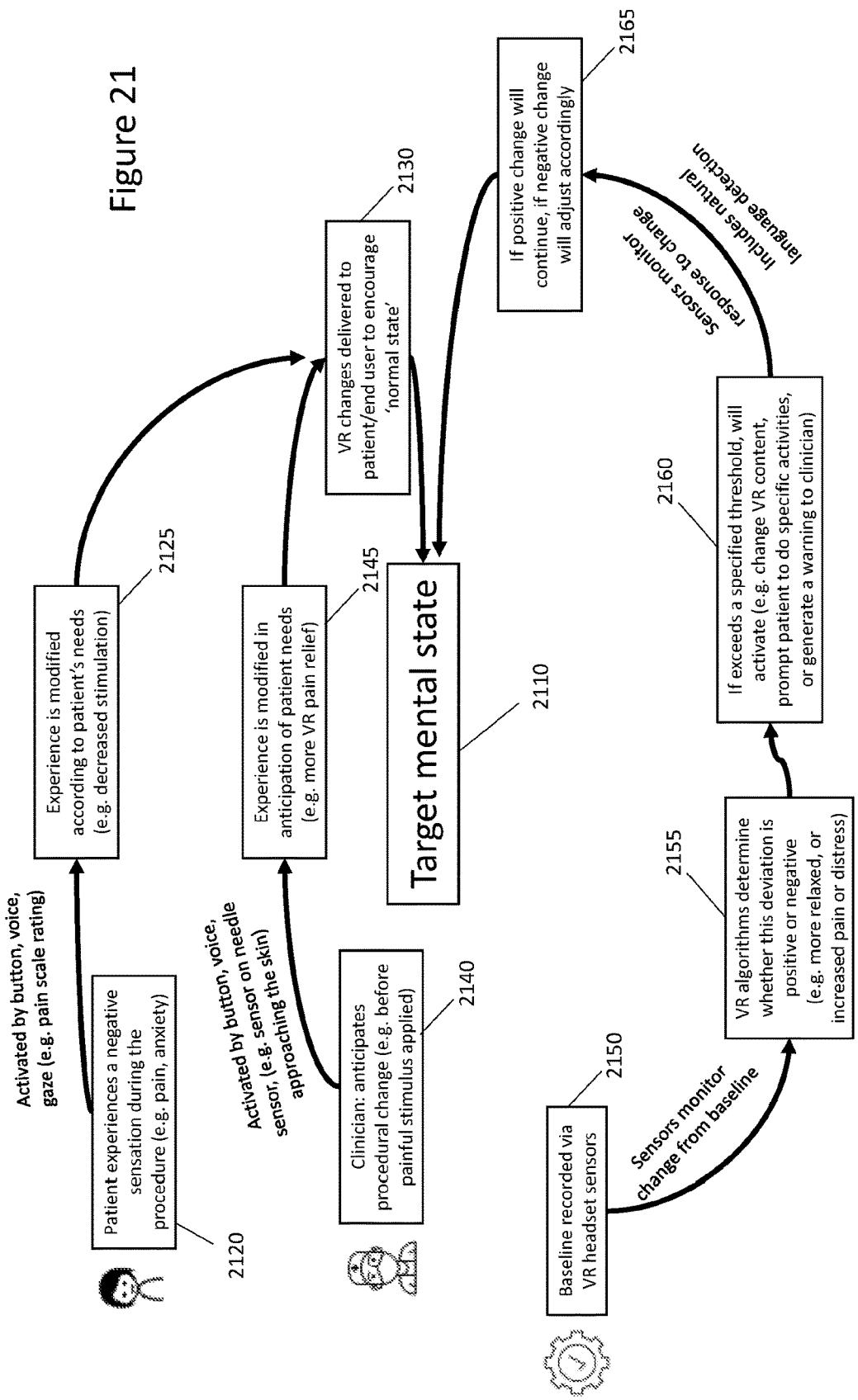
FIG. 21 illustrates diagrammatically feedback and modification loops for an embodiment of the system.

Embodiments of the VR system may be configured to allow modification of the VR experience dynamically during a procedure. In some embodiments VR experiences can be modified during delivery of the VR experience, FIG. 21 illustrates diagrammatically feedback and modification loops for an embodiment of the system. The objective of the feedback loops is to modify the VR experience to achieve a target mental state—for example calm and substantially pain free (although this may not be possible in all circumstances). It should be appreciated that some embodiments may implement only a selection (or none) of the modification options shown in FIG. 21.

Manual modification of experiences can be based on data feedback and may be influenced by the operator and wearer's interactions. In an embodiment the modification process is a dual-approach where both patient and clinician have choices and can initiate changes (manual) as well as automatic adjustments (e.g. biofeedback, sensors).

For example, from the perspective of patient experience the patient may be able to choose content (i.e. theme for VR experience) according to personal interests/preferences. The patient may also be able to choose the extent to which they will be immersed in the VR/AR experience. For example, for adult patients less immersion may be desirable. The option of the level of immersion may be discussed with the clinician in preparation for the procedure. Once the procedure is started with the VR experience initiated, if the patient has a negative sensation, i.e. anxiety or pain, 2120 the user can trigger a VR modification and the experience is modified 2125 according to the patient's needs. For example, this may be a change in scenario or alteration of the VR transpositions to increase the degree of modulation of sensation perceptions. The patient may also be able to adapt the level of immersion—for example becoming more immersed in the VR experience—if they wish to during the procedure, for example if they change their mind about being able to observe the procedure (with or without AR) or to increase the distraction and reduce pain perception. These changes are delivered to the patient to encourage a normal state 2130 and target mental state 2110. After a modification the feedback loop can be executed again if further modification is needed. In some embodiments for reframing pain: the VR uses algorithms around pain modulation and grading based on feedback from:

Biofeedback: sensors, warnings (see biofeedback section below)

Natural language detection: algorithms that select stimuli and content changes depending on response of what the patient is saying (distress, particular objects, colours, etc).

This provides personalised modulation: physical/emotional/ psychological pain, anxiety/distress—detect and support patient through the procedure. Some embodiments of the system can also use paired devices that can provide physical distraction (touch, sound, or be seen in AR as specific objects). For an AR implementation the patient is able to see some parts of their 'real' environment, but this is modified through AR. For example, the proceduralist may look different, a needle sensor can be used to enable tracking of the needle via the VR device so to the patient the needle is not seen but rather shown through VR as a fish approaching the patient.

The clinician may manually adjust the VR experience in anticipation of a procedural change 2140 for example before a painful part of the procedure or increased stimulus. Alternatively, the modification may be triggered by sensing of changes in the environment, such as proximity of needles to the skin or movement of the clinician. The experience is modified in anticipation of the patient needs 2145 and the changes are delivered to the patient 2130 to encourage maintaining or attaining the target mental state.

From the perspective of the clinician experience Using biofeedback the clinician is able to detect and pre-empt patients/clinicians around vasovagal episodes: e.g. heart rate deceleration. Other biofeedback such as pupil dilation, resting EMG, single-lead ECG, facial movements and processing time can indicate patient responsiveness and pain reactions. Other biofeedback can include skin conductance, heart rate (e.g. by oximetry), EMG. Another modification may be in response to ambient noise detection and modifying volume for the VR experience up or down in response. For example, to block out or screen ambient noises such as dentist drills or suction.

In addition to biofeedback being useful to the clinician, embodiments can also utilise biofeedback to trigger automatic modification of the VR experience. For example, a biofeedback monitoring baseline for the patient can be established 2150 and then the VR system monitors biofeedback (i.e. pupil dilation, facial movements, patient noises monitored via the device or biofeedback from other equipment such as ECG) for changes from the baseline, analysed automatically using an algorithm 2155 to determine if the changes indicate positive or negative patient responses to the VR experience. If the variation exceeds a threshold the VR experience may be automatically modified 2160, for example if the patient is becoming too relaxed to be alert for a step of the procedure requiring presence and cognitive response from the patient the patient may be prompted to interact with or be stimulated by the VR experience (for example to answer a question or say hello to a new character), a warning may also be issued to the clinician for example via a light/change to the externally visible display or audible alert. Alternatively, the VR experience may be automatically modified to increase modulation of pain or anxiety responses if a negative indication threshold is exceeded. If the patient reaction to the change is positive, then the change may be continued 2165 aiming to achieve a target mental state 2110.

Embodiments of the VR system may be configured to enable screening tests via telemetry. For example, to remotely monitor a patient using VR for procedure simulations. The VR device may be configured to transmit data captured during the VR experience, in real time or after conclusion of the VR experience, to a clinician or for inclusion in an electronic medical record. This data may be utilised to assess patient compliance for specific procedures (e.g. staying still for MRI scan, simulations, practicing or stretching out duration, response to desensitisation therapy, etc.). Capturing data from patient response to VR may also be input to tailoring VR experiences for continuing procedures, for example understanding preferences for scenarios for VR experiences or understanding of the modulation gradient for the individual for different VR transpositions. For example, recording positive pain transpositions and which transposition scenarios proved more or less effective. Also noting which scenarios may evoke negative anxiety responses (for example under water or flying) so these may be avoided for future VR experiences.

Embodiments of the VR system may also enable modulation of VR experiences based on feedback from the room, for example temperature, ambient noise, proximity of people or equipment to align the VR experience more closely with the environment or to mask environmental disturbances such as noise.

Modifications may also be based on previous healthcare data, for example from Electronic Medical Records (EMR), to provide personalised modification of VR experiences or procedures. For example, the EMR may provide historical information around successful cannulation sites, need for restraints, etc. to guide staff to increased procedural success.

Embodiments of the system may also be configured to utilise artificial intelligence (AI) or machine learning algorithms to analyse patient data from multiple procedures to understand success and risk factors for specific patient demographics, processes and procedures. Utilisation of AI may enable improved automation of patient specific customisation/personalisation of VR experiences.

The transposition of sensations can be modified during the VR experience both manually and based on automated feedback loops. This has an advantage of enabling the VR experience to change dynamically to best match the needs of the patient, procedure and clinician. Feedback loops function for both positive and negative feedback and respond accordingly.

Embodiments of the VR system can be used for pain management during medical procedures such as needles, other procedures, dental, dressings. In these procedures pain is managed via VR to remove the patient from experience, and or provide distractions. This enables the patients to get 'away' from the real environment, and reframe the physical sensation.

Some embodiments of the system may be utilised for personalised and adaptable VR treatment programs for phobias or rehabilitation. In these embodiments users can be immerse into experience to experience an environment which may induce or require confrontation of phobias using a graded approach. This may enable: Graded desensitisation of the feared object/scenario; the VR experience may automatically modify based on assessment of reactions as discussed above to increase or decrease the exposure to the phobia in the VR environment.

Embodiments may also be used for rehabilitation for example using VR for gamification, incentivisation—enabling users to get 'playful' in an environment for rehabilitation programs. This may include rehabilitation for specific medical conditions and physical exercise.

Embodiments of the VR system may also be used for Education both professional and consumer education programs. For example, VR experience may be set up for skills practice or testing skills for example diagnosis, identifying stroke or heart attack symptoms, or to develop knowledge, for example learning about organs. VR may also be useful in medical, nursing and allied health education and training. Simulation environments for emergencies (e.g. disaster, wilderness), an emergency parent or patient education: e.g. how to respond to seizures, anaphylaxis. VR may also be useful for general patient education: e.g. how to use your puffer. Other applications can include relaxation, immersive movies or videos for meditation, wellness and mindfulness.

Examples of applications for the VR system are provided in the table below.

| Group | Key aims | Examples | User journey e.g. | Data inputs (Pre/During/Post) | Use (Alone/In-person physical/In-person remote) | Experience (auto/semi-auto/manual) | VR/AR |
|---|---|---|---|---|---|---|---|
| Medical | Remove from experience | Needles, dental, wound dressings | Dental (e.g. cavity filling) | Pre & during Upload history Monitor during | In person (physical) | Semi-auto Foot pedals Language Biometric | VR |
| | Immerse in experience | Phobias, anxiety, new enviros | Phobias | Pre/during/post Natural language Visuals Time in experience Gaze direction | Alone | Auto/semi-auto | VR/AR (e.g. VR: see a virtual comical spider that slowly morphs into a real one, AR: object on table → hand) |
| | Train in experience | Rehabilitation, patient suitability testing (e.g. MRI) | Rehabilitation | Pre/during/post | Any use scenario | Any Physio increases reps or weight Patient responds to task | VR/AR (e.g. AR-learning to open a real door, twisting a jar) |
| | Diagnostics | Parkinson's disease, driving safety | Parkinson's disease | During/post Gaze Biometrics Natural language Diagnosis, severity, concerns | In person (physical)-we don't want self-diagnosis | Fully automated | VR/AR |
| Education | Knowledge | Organ anatomy, cell physiology, pharmaceutical development | Organ anatomy | None (just for learning purposes-see testing for assessment) | Alone | Manual (e.g. being able to turn the organ around, dissect) | VR/AR |

-continued

| Group | Key aims | Examples | User journey e.g. | Data inputs (Pre/During/Post) | Use (Alone/In-person physical/In-person remote) | Experience (auto/semi-auto/manual) | VR/AR |
|---|---|---|---|---|---|---|---|
| | Practice (scenario) | Disaster management, resuscitation, trauma codes, consumer and parent/teacher training | Parent anaphylaxis or seizure training | During/post Info retention Ability to perform the motions | Alone (or in collaboration with a group) | Any | VR/AR |
| | Testing (scenario) | For professionals (examples as above) | Providing resuscitation/first aid support | Post data Results pass/fail Identify gaps and learning needs | Any | Auto/semi-auto To monitor reaction and response to specific events | VR/AR |
| Other | Wellness | Mindfulness, relaxation | — | | Alone | — | VR/AR |
| | Empathy | Dementia, vision impairment | — | | Alone | — | VR/AR |

It will be understood to persons skilled in the art of the invention that many modifications may be made without departing from the spirit and scope of the invention.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A virtual reality device configured to be head mountable to a wearer and to allow device control via a device user interface accessible to an operator other than the wearer, to allow the operator to control device calibration and virtual reality (VR) experience start while the apparatus is worn by the wearer, and to provide one or more VR experiences each associated with a physical procedure, wherein at least one of the one or more VR experiences is designed to facilitate re-imagining of one or more physical sensations experienced by the wearer during the procedure, by each VR experience being choreographed with the physical procedure to, for each of the one or more physical sensations, provide a creative scenario which characterizes the physical sensation in an alternative way, to thereby transpose the perception of the physical sensation to something less painful or intimidating, wherein the VR experience is generated using a VR continuum experience framework comprising an order of execution for actions of a physical procedure incorporating at least one procedural action associated with a physical sensation and potentially inducing a pain response, and for each of the procedural actions potentially inducing a pain response defining characteristics of a VR transposition to modify perception for the action of pain, and wherein the virtual reality continuum (VR) experience framework for generating a VR continuum experience choreographed to a physical procedure incorporating at least one procedural action associated with a physical sensation and potentially inducing an anxiety or pain response, comprises:

an order of execution of the procedural actions; and for each of the procedural actions defining characteristics of a VR transposition to modify perception for the action of any one or more of pain, anxiety or presence.

2. A virtual reality device as claimed in claim 1 wherein the device is configured to perform calibration for the wearer and start a VR experience in response to a single initialization input from the operator.

3. A virtual reality device as claimed in claim 2 wherein the VR experience is selected by the operator via the device user interface before the initialization input.

4. A virtual reality device as claimed in claim 2 wherein the VR experience is predefined.

5. A virtual reality device as claimed in claim 2 wherein the device user interface is provided on the head mountable device.

6. A virtual reality device as claimed in claim 1 wherein the VR experience includes contextual reframing of sensations experienced by the wearer during the physical procedure.

7. A virtual reality device as claimed in claim 6 wherein the VR experience is further designed to coordinate timing of an operator for the physical procedure with the VR experience.

8. A virtual reality device as claimed in claim 7 wherein the VR experience and physical procedure timing is influenced by the wearer's interaction with the VR experience.

9. A virtual reality device as claimed in claim 1 wherein the device comprises a mobile phone providing processing, memory, visual display, motion sensing, audio and user interface functionality and a headset supporting the mobile phone, and wherein the mobile phone is loaded with a VR software application configured to restrict functions of the mobile phone to the VR functionality while the VR software application is executing.

10. A virtual reality device as claimed in claim 9 wherein the VR software application is configured to provide a touchscreen user interface displayed concurrently with a VR experience display and the headset is configured to prevent view of the touchscreen user interface by the user.

11. A virtual reality device as claimed in claim 1 wherein each VR transposition is any one or more of:
- defined based on the requirements of the procedure for presence and aspects of the action inducing physical sensation, and target direction for modification in one or more of presence, anxiety and pain perception;
- characterized by reframing aspects of the physical interaction in a manner which is not inconsistent with the physical sensation induced by the action and encourages altered perception of the physical sensation; and
- characterized by mimicking duration and attributes of the physical sensation for choosing a representation in a VR context using an interaction which is typically associated with less pain or anxiety than the actual physical action.

12. A virtual reality device as claimed in claim 11 wherein a VR experience is generated by selecting, from a library of VR experience components of a common theme, for each defined VR transposition a VR experience component fulfilling the characteristics of the defined VR transposition and compiling the selected VR experience components into a VR experience based on the action sequence for the procedure.

13. A virtual reality device as claimed in claim 1 wherein the VR experience is an experience on a VR continuum, the VR continuum including mixed reality or augmented reality (AR) allowing some real world perception and interaction well as total immersion VR.

\* \* \* \* \*